US012788971B2

(12) United States Patent
Broyles et al.

(10) Patent No.: US 12,788,971 B2
(45) Date of Patent: Nov. 10, 2026

(54) APPARATUSES, SYSTEMS, AND METHODS FOR PERCUTANEOUS DELIVERY OF NEUROSTIMULATION ARRAYS

(71) Applicant: W. L. Gore & Associates, Inc., Newark, DE (US)

(72) Inventors: Stuart E. Broyles, Flagstaff, AZ (US); Edward H. Cully, Clarksville, VA (US); Jeffrey B. Duncan, Flagstaff, AZ (US); Mark D. Edmundson, Rancho Palos Verdes, CA (US); Nathan L. Friedman, Flagstaff, AZ (US); Edward E. Shaw, Flagstaff, AZ (US); Christopher J. Vecchio, Philadelphia, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 288 days.

(21) Appl. No.: 18/287,404

(22) PCT Filed: Apr. 14, 2022

(86) PCT No.: PCT/US2022/024864
§ 371 (c)(1),
(2) Date: Oct. 18, 2023

(87) PCT Pub. No.: WO2022/225789
PCT Pub. Date: Oct. 27, 2022

(65) Prior Publication Data

US 2024/0198093 A1 Jun. 20, 2024

Related U.S. Application Data

(60) Provisional application No. 63/176,690, filed on Apr. 19, 2021.

(51) Int. Cl.
*A61N 1/05* (2006.01)

(52) U.S. Cl.
CPC .................................. *A61N 1/0553* (2013.01)

(58) Field of Classification Search
CPC . A61N 1/0553; A61N 1/0558; A61N 1/36062
See application file for complete search history.

(56) References Cited

U.S. PATENT DOCUMENTS 3,724,467 A 4/1973 Avery et al.
4,285,347 A 8/1981 Hess
(Continued)

FOREIGN PATENT DOCUMENTS

AU 2012200396 A1 2/2012
AU 2014202705 A1 6/2014
(Continued)

OTHER PUBLICATIONS

US 9,278,216 B2, 03/2016, Khalil et al. (withdrawn)
(Continued)

*Primary Examiner* — Eugene T Wu

(57) ABSTRACT

Embodiments of the present disclosure relate to apparatuses, systems, and methods for percutaneous delivery of neurostimulation arrays. In an embodiment, neurostimulation lead comprises a body portion configured to transition from a collapsed delivery configuration to an expanded deployed configuration. In aspects, the expanded deployed configuration is wider than the collapsed delivery configuration. Additionally, in some embodiments, transitioning the neurostimulation lead from the collapsed delivery configuration to the expanded deployed configuration comprises unfolding or unwrapping motions that are not perpendicular to the central axis of the delivery system. In certain embodiments, the neurostimulation lead includes an array of electrodes arranged on the body portion, wherein the array of elec-
(Continued)

trodes is electrically coupled to an implantable pulse generator (IPG).

7 Claims, 15 Drawing Sheets

(56) References Cited

U.S. PATENT DOCUMENTS 4,519,403 A 5/1985 Dickhudt
4,538,624 A 9/1985 Tarjan
4,549,556 A 10/1985 Tarjan et al.
4,590,949 A 5/1986 Pohndorf
4,658,835 A 4/1987 Pohndorf
5,095,905 A 3/1992 Klepinski
5,417,719 A 5/1995 Hull et al.
5,733,322 A 3/1998 Starkebaum
6,175,769 B1 1/2001 Errico et al.
6,205,361 B1 * 3/2001 Kuzma ................ A61N 1/0553 607/116
6,236,892 B1 5/2001 Feler
6,249,707 B1 6/2001 Kohnen et al.
6,266,568 B1 7/2001 Mann et al.
6,415,187 B1 7/2002 Kuzma et al.
6,510,347 B2 1/2003 Borkan
6,553,264 B2 4/2003 Redko et al.
6,606,521 B2 8/2003 Paspa et al.
6,901,287 B2 5/2005 Davis et al.
7,051,419 B2 5/2006 Schrom et al.
7,181,288 B1 2/2007 Rezai et al.
7,200,446 B2 4/2007 Borkan
7,333,857 B2 2/2008 Campbell
7,546,164 B2 6/2009 King
7,590,454 B2 9/2009 Garabedian et al.
7,603,178 B2 10/2009 North et al.
7,603,179 B1 10/2009 Grandhe
7,613,524 B2 11/2009 Jordan
7,640,064 B2 12/2009 Swoyer
7,672,734 B2 3/2010 Anderson et al.
7,736,576 B2 6/2010 Walter
7,769,472 B2 8/2010 Gerber
7,822,482 B2 10/2010 Gerber
7,894,911 B2 2/2011 Greenberg et al.
7,894,912 B2 2/2011 Benabid et al.
7,899,548 B2 3/2011 Barker
7,949,412 B1 5/2011 Harrison et al.
7,996,091 B2 8/2011 Harris
8,019,441 B2 9/2011 Wallace et al.
8,050,773 B2 11/2011 Zhu
8,090,450 B2 1/2012 Swoyer et al.
8,108,052 B2 1/2012 Boling
8,116,883 B2 2/2012 Williams et al.
8,135,477 B2 3/2012 Fattouh et al.
8,260,436 B2 9/2012 Gerber et al.
8,311,643 B2 11/2012 North
8,321,034 B2 11/2012 Weiss et al.
8,323,277 B2 12/2012 Vilims
8,359,101 B2 1/2013 Finch et al.
8,369,965 B2 2/2013 Skubitz et al.
8,412,350 B2 4/2013 Bly
8,442,649 B2 5/2013 Mcdonald
8,457,762 B2 6/2013 Schouenborg
8,463,403 B2 6/2013 Swanson
8,467,883 B2 6/2013 Chen et al.
8,486,089 B2 7/2013 Falkner et al.
8,532,788 B2 9/2013 Zhulati et al.
8,554,342 B2 10/2013 Thacker et al.
8,606,367 B2 12/2013 Pianca et al.
8,620,450 B2 12/2013 Tockman et al.
8,634,893 B2 1/2014 Skubitz et al.
8,676,347 B2 3/2014 Finley et al.
8,694,124 B2 4/2014 Pianca et al.
8,706,257 B2 4/2014 Swanson
8,712,552 B2 4/2014 Boling et al.
8,738,110 B2 5/2014 Tabada et al.
8,738,154 B2 5/2014 Zdeblick et al.
8,751,004 B2 6/2014 Dimarco
8,774,940 B2 7/2014 Feler
8,874,235 B1 10/2014 Swoyer et al.
8,880,176 B2 11/2014 Boling et al.
8,880,191 B2 11/2014 Pyles et al.
8,903,508 B2 12/2014 Feler
8,918,179 B2 12/2014 Peterson et al.
8,942,812 B2 1/2015 Machado et al.
8,942,821 B2 1/2015 Barolat
8,954,165 B2 2/2015 Sharma et al.
8,983,624 B2 3/2015 Imran
9,079,018 B2 7/2015 Olsen
9,079,019 B2 7/2015 Crosby et al.
9,084,882 B1 7/2015 Raines
9,095,699 B2 8/2015 Rosenberg et al.
9,095,712 B2 8/2015 Lee
9,149,628 B2 10/2015 Wahlstrand et al.
9,162,055 B2 10/2015 Pianca et al.
9,162,056 B2 10/2015 Pianca
9,174,052 B1 11/2015 Nabutovsky et al.
9,211,406 B2 12/2015 Bornzin et al.
9,220,899 B2 12/2015 Cattaneo et al.
9,233,247 B2 1/2016 Jaax
9,238,132 B2 1/2016 Barker
9,248,303 B2 2/2016 Yomtov
9,263,172 B2 2/2016 Lotfi
9,352,147 B2 5/2016 Nguyen-Stella et al.
9,358,390 B2 6/2016 Polefko et al.
9,358,396 B2 6/2016 Holley
9,393,422 B2 7/2016 Moffitt et al.
9,433,787 B2 9/2016 Elias et al.
9,440,076 B2 9/2016 Khalil et al.
9,492,664 B2 11/2016 Peterson
9,561,369 B2 2/2017 Burnes et al.
9,586,039 B2 3/2017 Bornzin et al.
9,616,219 B2 4/2017 De et al.
9,629,658 B2 4/2017 Barker
9,687,649 B2 6/2017 Thacker
9,700,736 B2 7/2017 Seymour et al.
9,844,661 B2 12/2017 Franz et al.
9,907,475 B2 3/2018 Kipke et al.
9,919,150 B2 3/2018 Krishnan et al.
9,937,342 B2 4/2018 Skelton et al.
9,950,164 B2 4/2018 Lipani
9,962,543 B2 5/2018 Feler et al.
9,974,946 B2 5/2018 Glenn et al.
9,993,649 B2 6/2018 Astrom et al.
10,076,382 B2 9/2018 Ku et al.
10,124,161 B2 11/2018 Barker
10,130,274 B2 11/2018 Voros et al.
10,238,874 B2 3/2019 Perryman et al.
10,258,789 B2 4/2019 Tischendorf et al.
10,315,034 B2 6/2019 Hou et al.
10,369,354 B2 8/2019 Barner
10,376,311 B2 8/2019 Zarins et al.
10,376,689 B2 8/2019 Kent et al.
10,420,938 B2 9/2019 Zhu et al.
10,434,312 B2 10/2019 Goel
10,449,374 B2 10/2019 Oron et al.
10,512,504 B2 12/2019 Chang et al.
10,524,832 B2 1/2020 Masson
10,583,285 B2 3/2020 Liu et al.
10,583,291 B2 3/2020 Biele et al.
10,583,295 B2 3/2020 Gupte et al.
10,603,484 B2 3/2020 Bakker et al.
10,603,485 B2 3/2020 Nageri
10,617,871 B2 4/2020 Ranu
10,668,274 B2 6/2020 Mitchell
10,675,457 B2 6/2020 Moffitt et al.
10,722,703 B2 7/2020 Mitchell
10,751,527 B2 8/2020 Wolf, II
10,758,724 B2 9/2020 Koop et al.
10,786,671 B2 9/2020 Voit et al.
10,987,638 B2 4/2021 Hollenbaugh et al.
2001/0023367 A1 * 9/2001 King ........................ A61N 1/05 607/117
2002/0111661 A1 8/2002 Cross et al.
2003/0078633 A1 4/2003 Firlik et al.
2003/0208247 A1 11/2003 Spinelli et al.

(56) References Cited

U.S. PATENT DOCUMENTS

| | | | |
|---|---|---|---|
| 2005/0033393 | A1 | 2/2005 | Daglow |
| 2005/0203604 | A1 | 9/2005 | Brabec et al. |
| 2006/0041295 | A1 | 2/2006 | Osypka |
| 2006/0127158 | A1 | 6/2006 | Olson et al. |
| 2006/0167525 | A1 | 7/2006 | King |
| 2007/0118198 | A1 | 5/2007 | Prager |
| 2007/0123766 | A1 | 5/2007 | Whalen et al. |
| 2007/0173914 | A1 | 7/2007 | Kollatschny |
| 2007/0197892 | A1 | 8/2007 | Shen et al. |
| 2007/0239242 | A1 | 10/2007 | Graubert |
| 2008/0027525 | A1 | 1/2008 | Frericks et al. |
| 2008/0140152 | A1 | 6/2008 | Imran et al. |
| 2008/0147158 | A1 | 6/2008 | Zweber et al. |
| 2008/0188917 | A1 | 8/2008 | Gerber et al. |
| 2008/0228250 | A1 | 9/2008 | Mironer |
| 2009/0062894 | A1 | 3/2009 | Stahmann et al. |
| 2009/0112301 | A1 | 4/2009 | Kowalczyk |
| 2010/0004721 | A1 | 1/2010 | Bryce et al. |
| 2010/0023102 | A1 | 1/2010 | Spruit |
| 2010/0057177 | A1 | 3/2010 | Moffitt et al. |
| 2010/0057178 | A1 | 3/2010 | Simon |
| 2010/0070010 | A1 | 3/2010 | Simpson |
| 2010/0114283 | A1 | 5/2010 | King |
| 2010/0137938 | A1 | 6/2010 | Kishawi et al. |
| 2010/0179562 | A1 | 7/2010 | Linker et al. |
| 2010/0292769 | A1 | 11/2010 | Brounstein et al. |
| 2010/0318167 | A1 | 12/2010 | Conn et al. |
| 2011/0077660 | A1 | 3/2011 | Janik et al. |
| 2011/0093036 | A1 | 4/2011 | Mashiach |
| 2011/0201984 | A1 | 8/2011 | Dubrow et al. |
| 2011/0224682 | A1 | 9/2011 | Westlund et al. |
| 2011/0257504 | A1 | 10/2011 | Hendricks et al. |
| 2011/0288618 | A1 | 11/2011 | Glen et al. |
| 2012/0035684 | A1 | 2/2012 | Thompson et al. |
| 2012/0065701 | A1 | 3/2012 | Cauller |
| 2012/0143296 | A1* | 6/2012 | Pianca ................. A61N 1/0553 607/116 |
| 2013/0018445 | A1 | 1/2013 | Sakai et al. |
| 2013/0041445 | A1 | 2/2013 | Erickson et al. |
| 2013/0060313 | A1 | 3/2013 | Cross, Jr. |
| 2013/0066331 | A1 | 3/2013 | Chitre et al. |
| 2013/0123866 | A1 | 5/2013 | Mcdonald |
| 2013/0184789 | A1 | 7/2013 | Stett et al. |
| 2013/0206454 | A1 | 8/2013 | Cattaneo et al. |
| 2013/0245416 | A1 | 9/2013 | Yarmush et al. |
| 2013/0245739 | A1 | 9/2013 | Arber |
| 2013/0289683 | A1 | 10/2013 | Parker et al. |
| 2013/0289686 | A1 | 10/2013 | Masson et al. |
| 2014/0276925 | A1 | 9/2014 | Alves et al. |
| 2014/0288577 | A1 | 9/2014 | Robinson et al. |
| 2015/0005860 | A1 | 1/2015 | Howard et al. |
| 2015/0119790 | A1 | 4/2015 | Moffitt et al. |
| 2015/0142010 | A1 | 5/2015 | Min et al. |
| 2015/0150508 | A1 | 6/2015 | Glenn et al. |
| 2015/0165193 | A1 | 6/2015 | Imran |
| 2015/0224318 | A1 | 8/2015 | Min et al. |
| 2015/0251004 | A1 | 9/2015 | Imran et al. |
| 2015/0359590 | A1 | 12/2015 | O'Connell et al. |
| 2016/0030735 | A1 | 2/2016 | Ouchouche |
| 2016/0067494 | A1 | 3/2016 | Lipani |
| 2016/0129243 | A1 | 5/2016 | Zhao et al. |
| 2016/0166829 | A1 | 6/2016 | Pianca et al. |
| 2016/0213915 | A1 | 7/2016 | Amrani |
| 2016/0213916 | A1 | 7/2016 | De La Rama |
| 2016/0367797 | A1 | 12/2016 | Eckermann |
| 2017/0001009 | A1 | 1/2017 | Peterson |
| 2017/0080213 | A1 | 3/2017 | Wright et al. |
| 2017/0120056 | A1 | 5/2017 | Woods et al. |
| 2017/0157389 | A1 | 6/2017 | Tai et al. |
| 2017/0259057 | A1 | 9/2017 | Muessig et al. |
| 2017/0312499 | A1 | 11/2017 | Linker et al. |
| 2017/0361088 | A1 | 12/2017 | Dadd et al. |
| 2017/0368334 | A1 | 12/2017 | Macdonald et al. |
| 2018/0056078 | A1 | 3/2018 | Kashyap et al. |
| 2018/0092682 | A1 | 4/2018 | Lawinger et al. |
| 2018/0126155 | A1 | 5/2018 | Mclaughlin et al. |
| 2018/0154155 | A1 | 6/2018 | Keaveney et al. |
| 2018/0169405 | A1 | 6/2018 | Kent et al. |
| 2018/0177417 | A1 | 6/2018 | Kipke et al. |
| 2018/0207419 | A1* | 7/2018 | Imran .................. A61N 1/0556 |
| 2018/0229036 | A1 | 8/2018 | Harkema et al. |
| 2018/0256906 | A1 | 9/2018 | Pivonka et al. |
| 2018/0272124 | A1 | 9/2018 | Kibler et al. |
| 2018/0296827 | A1 | 10/2018 | Pianca et al. |
| 2019/0001122 | A1 | 1/2019 | Ganty et al. |
| 2019/0030339 | A1 | 1/2019 | Baru et al. |
| 2019/0069949 | A1 | 3/2019 | Vrba et al. |
| 2019/0126043 | A1 | 5/2019 | Cullen et al. |
| 2019/0134347 | A1 | 5/2019 | Taha et al. |
| 2019/0142325 | A1 | 5/2019 | Min et al. |
| 2019/0224475 | A1 | 7/2019 | Dubuclet |
| 2019/0255339 | A1 | 8/2019 | Lee et al. |
| 2019/0275330 | A1 | 9/2019 | Sabesan et al. |
| 2019/0282805 | A1 | 9/2019 | Schmidt et al. |
| 2019/0298417 | A1 | 10/2019 | Barrett et al. |
| 2019/0308010 | A1 | 10/2019 | Sunkeri et al. |
| 2019/0328423 | A1 | 10/2019 | Shiroff et al. |
| 2019/0329030 | A1 | 10/2019 | Flowers et al. |
| 2019/0336772 | A1 | 11/2019 | Kim et al. |
| 2019/0344070 | A1 | 11/2019 | Molnar et al. |
| 2019/0344075 | A1 | 11/2019 | Bloch et al. |
| 2019/0351221 | A1 | 11/2019 | Ganty et al. |
| 2019/0366077 | A1 | 12/2019 | Capogrosso et al. |
| 2020/0009374 | A1 | 1/2020 | Howard et al. |
| 2020/0009386 | A1 | 1/2020 | Mansell |
| 2020/0016398 | A1 | 1/2020 | Grigsby et al. |
| 2020/0030599 | A1 | 1/2020 | Pepin et al. |
| 2020/0038652 | A1 | 2/2020 | Lee et al. |
| 2020/0078587 | A1 | 3/2020 | Deer |
| 2020/0094300 | A1 | 3/2020 | Holmes et al. |
| 2020/0108247 | A1 | 4/2020 | Melius et al. |
| 2020/0129775 | A1 | 4/2020 | Molnar et al. |
| 2020/0155019 | A1 | 5/2020 | Esteller et al. |
| 2020/0155240 | A1 | 5/2020 | Parker et al. |
| 2020/0155833 | A1 | 5/2020 | Villarta |
| 2020/0164204 | A1 | 5/2020 | Masson et al. |
| 2020/0179684 | A1 | 6/2020 | Howard et al. |
| 2020/0188655 | A1 | 6/2020 | Nikkhah et al. |
| 2020/0197697 | A1 | 6/2020 | Luhrs et al. |
| 2020/0214627 | A1 | 7/2020 | Christian et al. |
| 2020/0222689 | A1 | 7/2020 | Seifert et al. |
| 2020/0230399 | A1 | 7/2020 | Zaidi et al. |
| 2020/0230421 | A1 | 7/2020 | Zaidi et al. |
| 2020/0254235 | A1 | 8/2020 | Rump |
| 2020/0269052 | A1 | 8/2020 | Masson et al. |
| 2020/0282214 | A1 | 9/2020 | Boggs, II |
| 2021/0046305 | A1 | 2/2021 | Rosa et al. |

FOREIGN PATENT DOCUMENTS

| | | | |
|---|---|---|---|
| CN | 107029346 | A | 8/2017 |
| CN | 107252524 | A | 10/2017 |
| CN | 110947094 | A | 4/2020 |
| CN | 111450411 | A | 7/2020 |
| DE | 19758110 | A1 | 7/1999 |
| EP | 2389975 | A1 | 11/2011 |
| EP | 2742969 | A1 | 6/2014 |
| JP | 2011-512991 | A | 4/2011 |
| KR | 10-2020-0056327 | A | 5/2020 |
| WO | 2008/080073 | A2 | 7/2008 |
| WO | 2008/108758 | A1 | 9/2008 |
| WO | 2009/111142 | A2 | 9/2009 |
| WO | 2013/160173 | A1 | 10/2013 |
| WO | 2015/020945 | A2 | 2/2015 |
| WO | 2015/047817 | A1 | 4/2015 |
| WO | 2017/143189 | A1 | 8/2017 |
| WO | 2017/143192 | A2 | 8/2017 |
| WO | 2019/020983 | A1 | 1/2019 |
| WO | 2019/020984 | A1 | 1/2019 |
| WO | 2019/178507 | A1 | 9/2019 |
| WO | 2019/232544 | A1 | 12/2019 |
| WO | 2020/036886 | A1 | 2/2020 |

(56) References Cited

FOREIGN PATENT DOCUMENTS

| | | | |
|---|---|---|---|
| WO | 2020/069567 | A1 | 4/2020 |
| WO | 2020/092652 | A1 | 5/2020 |
| WO | 2021/005382 | A1 | 1/2021 |

OTHER PUBLICATIONS

Ahmeda et al., "Burst and high frequency stimulation: underlying mechanism of action", Expert Review of Medical Devices, vol. 15, No. 1, 2018, pp. 61-70.

International Preliminary Report on Patentability received for PCT Patent Application No. PCT/US2022/024864, mailed on Nov. 2, 2023, 12 pages.

International Search Report and Written Opinion received for PCT Patent Application No. PCT/US2022/024864, mailed on Jul. 18, 2022, 20 pages.

Slavin et al., "Tonic and burst spinal cord stimulation waveforms for the treatment of chronic, intractable pain: study protocol for a randomized controlled trial", Trials, vol. 17, No. 569, 2016, pp. 1-11.

* cited by examiner

Distal-end views
213
206

Retract Exterior Delivery Sheath
202
206
208
212

Unwind to Deploy
202
206
212
212

Unwind to Deploy
202
206
208

Retract Slotted Deployment Sheath
202
208

Retract central rod
208

Depolyment Complete 1002
1006

1002
1006

1008A
1002
1008B 1002
1006

1016
1020A
1018A
1018B
1020B
1002
1008A
1008B 1002
1006

1010
1002
1012
1008
1014
1004
1016

1002
1006

APPARATUSES, SYSTEMS, AND METHODS FOR PERCUTANEOUS DELIVERY OF NEUROSTIMULATION ARRAYS

CROSS-REFERENCE TO RELATED APPLICATION

This application is a national phase application of PCT Application No. PCT/US2022/024864, internationally filed on Apr. 14, 2022, which claims the benefit of Provisional Application No. 63/176,690, filed Apr. 19, 2021, which are incorporated herein by reference in their entireties for all purposes.

FIELD

The present disclosure relates generally to apparatuses, systems, and methods for neurostimulation arrays. More specifically, the disclosure relates to apparatuses, systems, and methods for percutaneous delivery of neurostimulation arrays.

BACKGROUND

A spinal cord stimulator is an implanted device that electrically stimulates the spinal cord to relieve pain. Spinal cord stimulation is generally used after nonsurgical pain treatment options have failed to provide sufficient relief. Spinal cord stimulator systems have three main parts: (i) an array of electrodes located along the spinal cord in the epidural space, (ii) an implanted pulse generator (IPG), a pacemaker-like module that contains a battery and electronics to generate the required electrical waveforms, and (iii) an external controller located outside the body. The IPG is placed under the skin, usually near the buttocks or abdomen and wires run under the skin from the IPG to the electrode array. The controller allows patients and clinicians to turn off or adjust the stimulation waveform parameters. In instances, the controller may also wirelessly charge the battery in the implanted IPG.

SUMMARY

Embodiments disclosed herein improve upon conventional embodiments by disclosing an electrode array that can be delivered percutaneously and have a large coverage area.

According to one example ("Example 1"), a neurostimulation lead, comprises: a body portion configured to transition from a collapsed delivery configuration to an expanded deployed configuration, wherein the expanded deployed configuration is wider than the collapsed delivery configuration; and an array of electrodes arranged on the body portion, wherein the array of electrodes is electrically coupled to an implantable pulse generator (IPG).

According to one example ("Example 2"), the neurostimulation lead of Example 1, wherein a width of the body portion in the expanded deployed confirmation is configured to extend across a spinal cord and at least a portion of one or more dorsal root ganglion.

According to one example ("Example 3"), the neurostimulation lead of any one of Examples 1-2, wherein a width of the body portion is greater than 6 mm.

According to one example ("Example 4"), the neurostimulation lead of any one of Examples 1-3, wherein a width of the body portion is between 6 mm and 15 mm.

According to one example ("Example 5"), the neurostimulation lead of any one of Examples 1-4, wherein the body portion comprises a non-zero curvature when the body portion is in the expanded deployed configuration.

According to one example ("Example 6"), the neurostimulation lead of any one of Examples 1-5, wherein the body portion is in a rolled configuration while the body portion is in the collapsed delivery configuration and the body portion is an unrolled configuration while the body portion is in the expanded deployed configuration and to transition from the collapsed delivery configuration to the expanded deployed configuration, the body portion is configured to unroll.

According to one example ("Example 7"), the neurostimulation lead of any one of Examples 1-6, wherein the body portion comprises one or more stiffening members extended laterally across at least a portion of the body portion.

According to one example ("Example 8"), the neurostimulation lead of any one of Examples 1-7, configured to be delivered via a catheter comprising side slots and the body portion extends through the side slots to transition from the collapsed delivery configuration to the expanded deployed configuration.

According to one example ("Example 9"), the neurostimulation lead of any one of Examples 1-5 and 7-8, wherein the body portion is in a folded configuration while the body portion is in the collapsed delivery configuration and the body portion is an unfolded configuration while the body portion is in the expanded deployed configuration and to transition from the collapsed delivery configuration to the expanded deployed configuration, the body portion is configured to unfold.

According to one example ("Example 10"), the neurostimulation lead of any one of Examples 1-9, wherein the body portion comprises a central spine and a plurality of side supports.

According to one example ("Example 11"), the neurostimulation lead of any one of Examples 1-10, wherein when the body portion is in the expanded deployed configuration, the body portion has a coil shape.

According to one example ("Example 12"), the neurostimulation lead of any one of Examples 1-10, wherein when the body portion is in the expanded deployed configuration, the body portion has a serpentine shape.

According to one example ("Example 13"), the neurostimulation lead of any one of Examples 1-10, wherein when the body portion is in the expanded deployed configuration, the body portion has a winged shape.

According to one example ("Example 14"), the neurostimulation lead of any one of Examples 1-13, wherein the body portion incorporates a frame composed of a shape-memory material, wherein a relaxed shape of the shape-memory material is when the frame is the expanded deployed configuration.

According to one example ("Example 15"), the neurostimulation lead of Example 14, wherein the shape-memory material is nitinol.

According to one example ("Example 16"), the neurostimulation lead of any one of Examples 1-15, wherein the body portion forms an elastomeric sleeve.

According to one example ("Example 17"), the neurostimulation lead of any one of Examples 1-5, 7-8, and 10-16, wherein the body portion is in an uninflated configuration while the body portion is in the collapsed delivery configuration and the body portion is in an inflated configuration while the body portion is in the expanded deployed configuration and to transition from the collapsed delivery configuration to the expanded deployed configuration, the body portion is configured to be inflated.

According to one example ("Example 18"), the neurostimulation lead of Example 17, wherein the body portion is pneumatically inflated or hydraulically inflated.

According to one example ("Example 19"), the neurostimulation lead of any one of Examples 1-18, comprising of hardening agent to fix the body portion in the expanded deployed configuration.

According to one example ("Example 20"), the neurostimulation lead of any one of Examples 1-19, wherein the expanded deployed configuration is thinner than the collapsed delivery configuration.

According to one example ("Example 21"), the neurostimulation lead of any one of Examples 1-20, further comprising anchors to secure the body portion to a spine.

According to one example ("Example 22"), the neurostimulation lead of Example 21, wherein the anchors are barbs.

According to one example ("Example 23"), the neurostimulation lead of Example 21, wherein the anchors are configured to encourage tissue attachment to the anchors.

According to one example ("Example 24"), the neurostimulation lead of any one of Examples 1-23, wherein at least a portion of the neurostimulation lead is comprised of a material that encourages tissue ingrowth.

According to one example ("Example 25"), the neurostimulation lead of any one of Examples 1-24, further comprising the IPG.

According to one example ("Example 26"), the neurostimulation lead of Example 25, further comprising an external controller communicatively coupled to the IPG.

According to one example ("Example 27"), wherein the neurostimulation lead comprises a plurality of first portions that are thicker than a second portion of the neurostimulation lead, wherein the neurostimulation lead is arranged in a pattern such that the locations of at least one of the plurality of first portions do not overlap another first portion of the plurality of first portions.

According to one example ("Example 28"), wherein the plurality of first portions comprise the array of electrodes.

According to one example ("Example 29"), the neurostimulation lead of any one of Examples 1-28, wherein a cross-sectional area of solid material of the neurostimulation lead is smaller in the collapsed delivery configuration than in the expanded deployed configuration.

According to one example ("Example 30"), the neurostimulation lead of any one of Examples 1-29, wherein transitioning the neurostimulation lead from the collapsed delivery configuration to the expanded deployed configuration comprises unfolding or unwrapping motions that are not perpendicular to the central axis of the delivery system.

According to one example ("Example 31"), a method for implanting a neurostimulation lead within a subject, comprises: inserting a catheter percutaneously into the subject, wherein a distal end of the catheter is positioned adjacent to an implantation site within the subject, the implantation site being located within an epidural space of the subject; delivering the neurostimulation lead through the catheter to the implantation site while the neurostimulation lead is in a collapsed delivery configuration, the neurostimulation lead being according to one of Examples 1-30; and transitioning the neurostimulation lead from the collapsed delivery configuration to an expanded deployed configuration.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
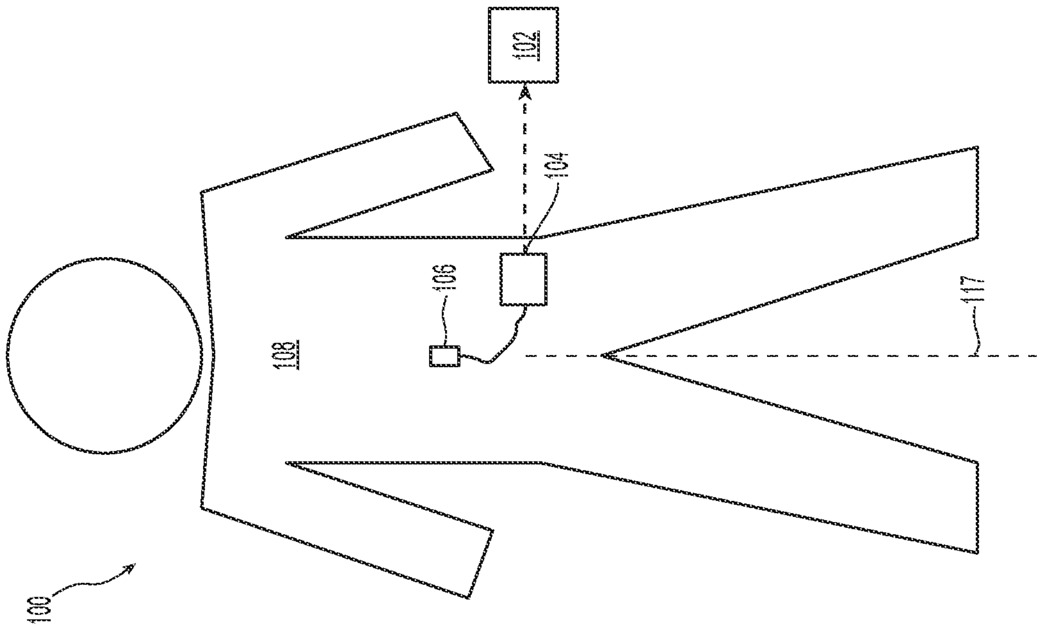
FIG. 1 is a diagram of a neuromodulation system, in accordance with at least some embodiments of the present disclosure.

This disclosure is not meant to be read in a restrictive manner. For example, the terminology used in the application should be read broadly in the context of the meaning those in the field would attribute such terminology.

With respect to terminology of inexactitude, the terms “about” and “approximately” may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms “about” and “approximately” can be understood to mean plus or minus 10% of the stated value.

DESCRIPTION OF VARIOUS EMBODIMENTS

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Most spinal cord stimulators require two procedures, one to test and one to implant the device: the trial and the implantation. In the trial period, a surgeon implants a temporary electrode array to determine how well the therapy will work for a given patient. The array may be composed of two flexible cylindrical leads with multiple electrodes along their length. One lead is placed on the right of the spinal column and one on the left. The leads are inserted percutaneously under fluoroscopic X-ray guidance. The location of the pain determines where the electrodes are placed along the spine. The trial procedure typically requires an incision in the lower back to place the electrodes. The trial implantable pulse generator (IPG) is located outside the body, typically on a belt worn around the waist. The trial period typically lasts from 4-7 days and allows the patient to evaluate how well the device reduces pain. The trial is considered a success if there is a 50% or greater reduction in pain level. At the end of the trial period the leads are removed. If the trial was successful, surgery is scheduled to permanently implant a device.

During the permanent implantation procedure, the IPG is placed underneath the skin in the upper buttock/back, upper chest wall, or abdominal area and the trial electrodes are replaced with either a set of percutaneous electrode leads similar to the ones used in the trial or with a surgically placed paddle electrode array. Percutaneous leads have a single column of electrodes axially distributed along the length of the active section of the lead. Paddle electrode arrays have a two-dimensional distribution of electrodes. The larger width and overall size of current paddle arrays means that they must be implanted via a surgical (versus minimally invasive) procedure, typically performed via laminectomy (removal of the back portion of a vertebra).

Compared to the surgical placement of a paddle electrode array, the placement of percutaneous electrode leads is a quicker, less invasive procedure. Also, the percutaneous procedure may be performed by anesthesiologists trained in pain management, spinal surgeons, or neurosurgeons, whereas a paddle array must be implanted by a surgeon. However, in comparison to a surgically placed paddle array, percutaneously placed leads have a limited coverage area, are more likely to migrate, and provide a less focused field of charge injection (which can limit pain targeting precision and negatively impact battery life).

Embodiments of the present disclosure provide solutions to these problems by disclosing a neurostimulation lead that can be delivered percutaneously while also covering a larger surface area than conventional percutaneously delivered leads due to being able to transition from a collapsed delivery configuration to an expanded deployed configuration, as discussed in more detail below. In certain aspects, the embodiments disclosed below corresponding to transitioning a neurostimulation lead from a collapsed delivery configuration to an expanded deployed configuration can be performed in reverse to transition the neurostimulation lead from an expanded deployed configuration to a collapsed delivery configuration to withdraw the lead from the subject and/or to reposition the lead during a procedure. For example, the neurostimulation lead can be arranged within a delivery device prior to implanting the neurostimulation lead and/or to withdraw and/or reposition the neurostimulation lead after and/or during implantation.

FIG. 1 is a diagram of a neuromodulation system 100, in accordance with at least some embodiments of the present disclosure. This diagram is merely an example, which should not unduly limit the scope of the claims. One of ordinary skill in the art would recognize many variations, alternatives, and modifications.

In the illustrated embodiment, the system 100 includes a controller 102, an implantable pulse generator (IPG) 104, and a neurostimulation lead 106 implanted within a subject 108. In certain embodiments, the neurostimulation lead 106 includes an array of electrodes implanted within an epidural space 132 of the subject (shown in more detail in FIGS. 2A and 2B). According to certain embodiments, the IPG 104 is electrically coupled to the neurostimulation lead 106 and includes one or more power sources and/or electrical components configured to generate and send one or more stimulating electrical waveforms to the neurostimulation lead 106, which are then transmitted to the subject’s 108 nervous system and produce therapeutic effects. In certain instances, the IPG 104 is implanted under the subject’s 108 skin near, for example, the subject’s 108 abdomen or buttocks. And, the IPG 104 is electrically coupled to the neurostimulation lead 106 via one or more wires placed under the subject's 108 skin.

According to certain embodiments, the controller 102 is wirelessly coupled to the IPG 106 and is configured to allow the subject 108 and/or a clinician to communicate with the IPG 106. In certain embodiments, the controller 102 can include a programming device that allows the subject 108 and/or a clinician to initialize and adjust settings for the IPG 106. For example, the controller 102 can allow the subject 108 and/or a clinician to turn off and/or adjust the stimulating electrical waveforms produced by the IPG 104. In certain instances, the controller 102 is configured to wirelessly charge the IPG 104.

According to certain embodiments, the neurostimulation lead 106 can include a collapsed delivery configuration for delivering the neurostimulation lead 106 percutaneously via a catheter to an implantation site. Once the neurostimulation lead 106 is located at the implantation site, the neurostimulation lead 106 can be deployed to an expanded deployed configuration. In certain embodiments, the expanded deployed configuration can be wider than the collapsed delivery configuration. Due to the wider expanded deployed configuration, the neurostimulation lead 106 is capable of stimulating a larger area than conventional neurostimulation leads that are implanted percutaneously. In addition, the neurostimulation lead 106 provides an advantage over larger neurostimulation leads that require laminectomy due to the neurostimulation lead 106 being able to be implanted percutaneously.

Additional details about the neurostimulation lead 106 and the collapsed delivery configuration and expanded deployed configuration of the neurostimulation lead 106 are described below. As set forth above, in certain aspects, the embodiments disclosed herein corresponding to transitioning a neurostimulation lead from a collapsed delivery configuration to an expanded deployed configuration can be performed in reverse to transition the neurostimulation lead 106 from the expanded deployed configuration to the collapsed delivery configuration.

Figure 2A:
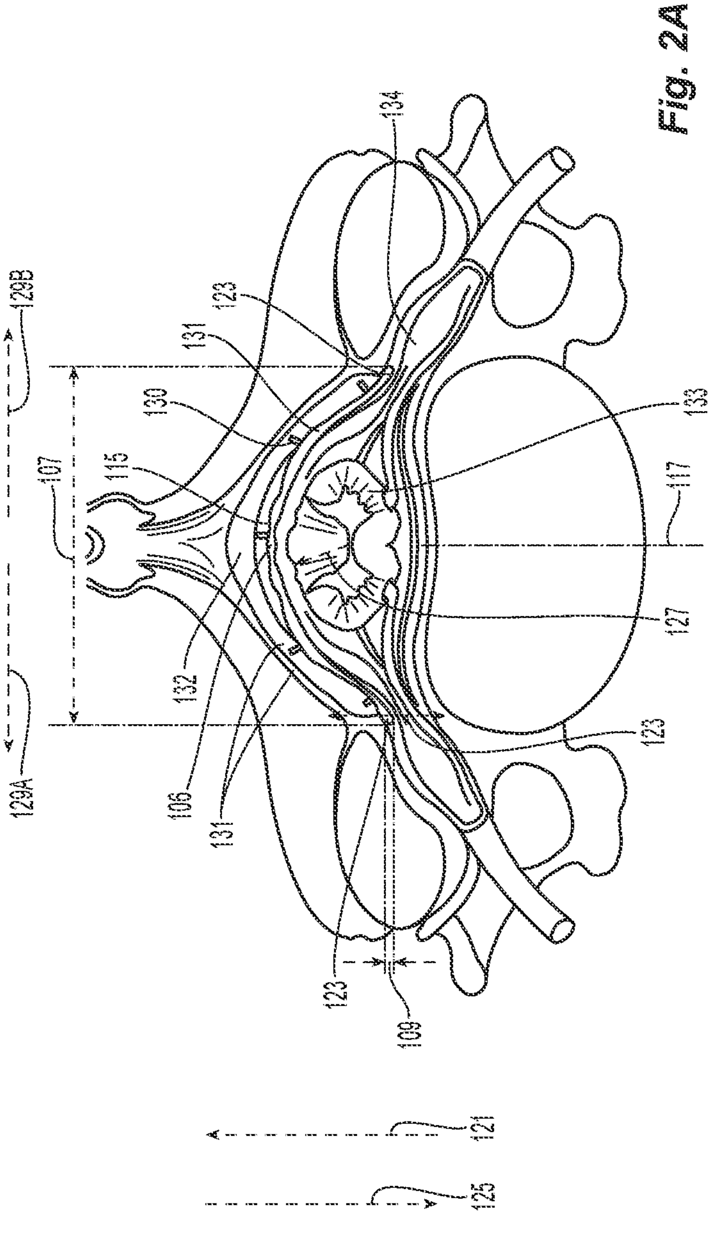
FIG. 2A is a cross-sectional view of a spinal column with a neurostimulation lead implanted within an epidural space of the spinal column and FIG. 2B is a perspective of the neurostimulation lead implanted within the epidural space, in accordance with at least some embodiments of the present disclosure.
Figure 2B:
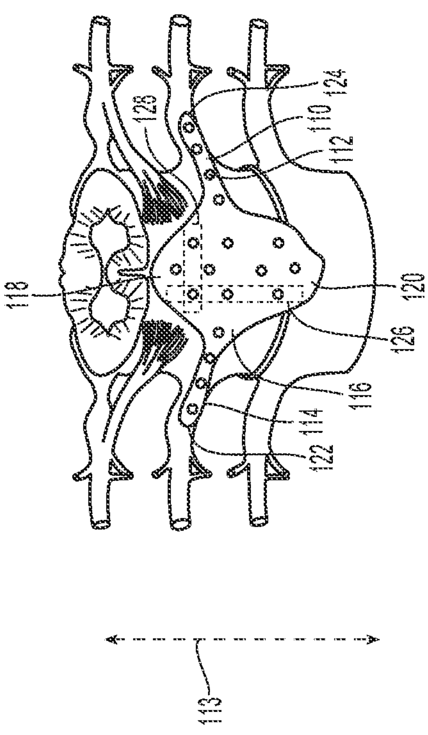

FIG. 2A is a cross-sectional view of a spinal column with a neurostimulation lead implanted within an epidural space 132 of the spinal column and FIG. 2B is a perspective of the neurostimulation lead 106 implanted within an epidural space 132. These diagrams are merely examples, which should not unduly limit the scope of the claims. One of ordinary skill in the art would recognize many variations, alternatives, and modifications. For example, the neurostimulation lead 106 has a winged shape, but this is only one embodiment and other examples are provided in the FIGs. below.

In the illustrated embodiment, the neurostimulation lead 106 is in an expanded deployed configuration. As shown, the neurostimulation lead 106 is implanted within the epidural space 132. In certain embodiments, the neurostimulation lead 106 includes a body portion 110 that is arranged near the centerline of the spinal cord 133, the left and right sides of the spinal cord 133 and/or a portion of at least one dorsal root ganglion 134. According to certain embodiments, the body portion 110 includes an array of electrodes 112 arranged on the body portion 110. The array of electrodes 112 can be coupled to an IPG (e.g., IPG 104) in order to receive electrical waveforms from the IPG and deliver the waveforms to stimulate the left and right sides of the spinal cord 133 and/or dorsal root ganglion 134.

According to certain embodiments, the neurostimulation lead 106 has a width 107 when the neurostimulation lead 106 is in an expanded deployed configuration that is greater than a width when the neurostimulation lead 106 is in a collapsed delivery configuration. According to certain embodiments, the width 107 of the neurostimulation lead 106 is measured in a direction perpendicular to the longitudinal axis 113 of the neurostimulation lead 106. In certain instances, once the neurostimulation lead 106 is implanted, at least a portion of the width 107 (e.g., a central portion 115) extends perpendicular to the sagittal plane 117 and parallel to the coronal plane of the person within which neurostimulation lead 106 is implanted.

In an embodiment, the width 107 of the neurostimulation lead 106 is greater than 6 mm. In another embodiment, the width 107 of the neurostimulation lead 106 is greater than 7 mm. In even another embodiment, the width 107 of the neurostimulation lead 106 is greater than 8 mm. In yet another embodiment, the width 107 of the neurostimulation lead 106 is greater than 9 mm. In even yet another embodiment, the width 107 of the neurostimulation lead 106 is greater than 10 mm. In another embodiment, the width 107 of the neurostimulation lead 106 is greater than 11 mm. In even another embodiment, the width 107 of the neurostimulation lead 106 is greater than 12 mm. In yet another embodiment, the width 107 of the neurostimulation lead 106 is greater than 13 mm. In even yet another embodiment, the width 107 of the neurostimulation lead 106 is greater than 14 mm.

According to certain embodiments, the width 107 of the neurostimulation lead 106 is between 6 mm and 15 mm. In another embodiment, the width 107 of the neurostimulation lead 106 is between 7 mm and 15 mm. In even another embodiment, the width 107 of the neurostimulation lead 106 is between 8 mm and 15 mm. In yet another embodiment, the width 107 of the neurostimulation lead 106 is between 9 mm and 15 mm. In even yet another embodiment, the width 107 of the neurostimulation lead 106 is between 10 mm and 15 mm. In another embodiment, the width 107 of the neurostimulation lead 106 is between 11 mm and 15 mm. In even another embodiment, the width 107 of the neurostimulation lead 106 is between 12 mm and 15 mm. In yet another embodiment, the width 107 of the neurostimulation lead 106 is between 13 mm and 15 mm. In even yet another embodiment, the width 107 of the neurostimulation lead 106 is between 14 mm and 15 mm.

Figures 3A, 3B, 3C, 3D, 3E, 3F, 3G:
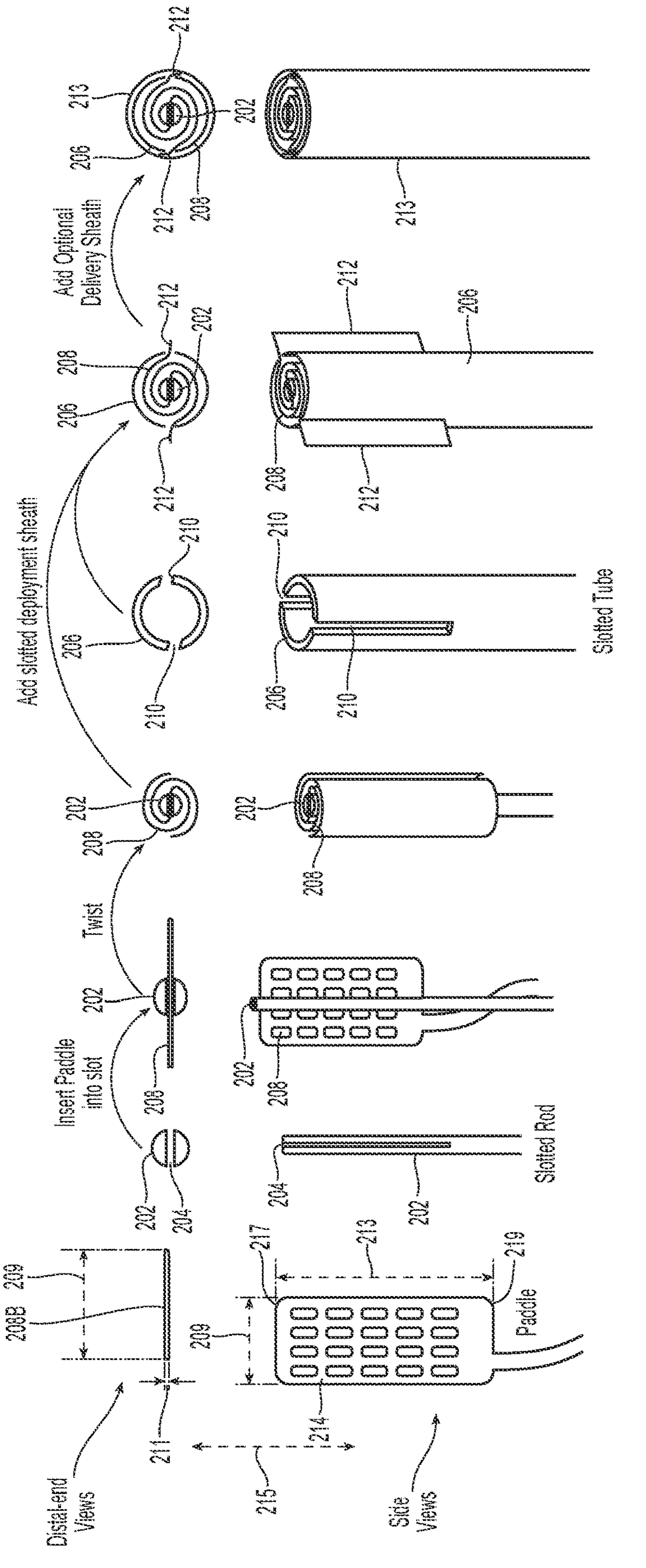
FIGS. 3A-3M are side views and distal-end views of an example delivery device and a neurostimulation lead transitioning from a collapsed delivery configuration to an expanded deployed configuration, in accordance with at least some embodiments of the present disclosure.

Additionally, or alternatively, the neurostimulation lead 106 has a cross-sectional thickness 109 that when the neurostimulation lead 106 is in an expanded deployed configuration (shown in FIG. 2A) is less than when the neurostimulation lead 106 is in a collapsed delivery configuration (see, e.g., FIG. 3D). According to certain embodiments, the cross-sectional thickness 109 can be measured as a height of the neurostimulation lead 106 along a line 117 that bisects the sagittal plane of the neurostimulation lead 106, wherein the line 117 extends parallel to the sagittal plane. Additionally, or alternatively, in certain embodiments, the cross-sectional area of the neurostimulation lead 106 is smaller in the collapsed delivery configuration than in the expanded deployed configuration. In at least some embodiments, the cross-sectional thickness 109 and the cross-sectional area is taken perpendicular/transverse to the longitudinal axis 113. In certain instances, the longitudinal axis 113 may be referred to as a central axis of, for example, a delivery system of the neurostimulation lead 106 and/or the neurostimulation lead 106.

According to certain embodiments, the neurostimulation lead 106 can be curved when the neurostimulation lead 106 is in the expanded deployed configuration to conform to the anatomy (e.g., the spinal cord 133) of a subject 108, as illustrated in FIG. 2A. In these instances, a central portion 115 can be arranged in a posterior direction 121 relative to the ends 123 such that the ends 123 are arranged in an anterior direction 125 relative to the central portion 115. Additionally, or alternatively, the neurostimulation lead 106 can include a non-zero curvature 127 when the neurostimulation lead 106 is in an expanded deployed configuration, as shown in FIG. 2A. In some embodiments, the non-zero curvature may be the reciprocal of the radius of curvature. In some instances, the non-zero curvature 127 is configured so that the neurostimulation lead 106 conforms to the spinal cord 133. In some instances, the non-zero curvature 127 can increase as the neurostimulation lead 106 extends in a lateral direction 129 away from the central portion 115. Further, in some examples, the neurostimulation lead 106 can include an inflection point 131 such that the neurostimulation lead 106 curves in a direction opposite the non-zero curvature 127, as the neurostimulation lead 106 extends in a lateral direction 129 away from the inflection point 131.

According to certain embodiments, one or more electrodes of the array of electrodes 112 can be arranged near a perimeter 114 of the body portion 110. Additionally, or alternatively, one or more electrodes of the array of electrodes 112 can be arranged away from the perimeter 114 of the body portion 110 near, for example, a central portion 116 of the body portion 110. Additionally, or alternatively, one or more electrodes of the array of electrodes 112 can be arranged near a distal portion 118, a proximal portion 120, a left portion 122, and/or a right portion 124 of the body portion 110. In certain embodiments, one or more of the electrodes of the array of electrodes 112 can be arranged in one or more columns, for example, column 126. Additionally, or alternatively, one or more of the electrodes of the array of electrodes 112 can be arranged in one or more rows, for example, row 128. Each column 126 and/or row 128 can include multiple electrodes.

According to certain embodiments, due to the wide coverage area of the body portion 110 and/or the array of electrodes 112, the neurostimulation lead 106 can provide better stimulation and/or more accurate stimulation than a narrower neurostimulation lead. As explained in more detail below, the body portion 110 is wider when in an expanded deployed configuration (shown) than when the body portion 110 is in a collapsed delivery configuration. As such, the neurostimulation lead 106 can be delivered percutaneously while the neurostimulation lead 106 is in a collapsed delivery configuration, providing for less invasive implantation than conventional embodiments.

In certain embodiments, the neurostimulation lead 106 can be formed from and/or coated by a biocompatible material. In certain instances, the neurostimulation lead 106 may include polyethylene (PE), expanded PE (ePE), and/or a fluoropolymer, such as a polytetrafluoroethylene (PTFE) polymer or an expanded polytetrafluoroethylene (ePTFE) polymer. In some instances, the neurostimulation lead 106 may be formed of, at least in part, a polyester, a silicone, a urethane, a polyethylene terephthalate, or another biocompatible polymer, or combinations thereof. In some instances, bioresorbable or bioabsorbable materials may be used, for example a bioresorbable or bioabsorbable polymer. In some instances, the neurostimulation lead 106 may be formed of, at least in part, Dacron, polyethylene (PE), expanded PE (ePE), polyolefins, carboxy methylcellulose fabrics, polyurethanes, or other woven, non-woven, or film elastomers.

According to certain embodiments, the neurostimulation lead 106 includes a frame constructed from a shape-memory material. In some instances, the frame is in a relaxed shape when the neurostimulation lead 106 is an in expanded deployed configuration. For example, nitinol (NiTi) may be used as the material of the frame (and any of the frames discussed herein) of the neurostimulation lead 106, but other materials such as, but not limited to, stainless steel, L605 steel, polymers, MP35N steel, Pyhnox, Elgiloy, or any other appropriate biocompatible material, and combinations thereof, can be used as the material of the frame. The super-elastic properties and softness of NiTi may enhance the conformability of the frame. In addition, NiTi can be shape-set into a desired shape. That is, NiTi can be shape-set so that the frame tends to self-expand into a desired shape when the frame is unconstrained, such as when the frame is deployed out from a delivery system. Stated another way, the neurostimulation lead 106 can be collapsed when being delivered through a catheter and once the neurostimulation lead 106 is positioned at the implantation site (e.g., within the epidural space 132), the catheter can be withdrawn and the neurostimulation lead 106 will expand to the deployed position due to the original shape of the NiTi frame.

According to certain embodiments, the neurostimulation lead 106 can be inflatable. By inflating the neurostimulation lead 106, the neurostimulation lead 106 can transition from a collapsed delivery configuration to an expanded deployed configuration. In certain aspects, the neurostimulation lead 106 can be pneumatically and/or hydraulically inflated using, for example, a hydrogel. In certain embodiments, the neurostimulation lead 106 can be deflated to transition the neurostimulation lead 106 from an expanded deployed configuration to the collapsed delivery configuration.

According to certain embodiments, the neurostimulation lead 106 can include a hardening agent so that when the neurostimulation lead 106 is in an expanded deployed configuration, the hardening agent can fix the neurostimulation lead 106 in the expanded deployed configuration to reduce the likelihood the neurostimulation lead 106 compresses and/or expands and/or migrates as the subject 108 moves, bends, twists, etc. In certain embodiments, the hardening agent can be injected into the neurostimulation lead 106.

According to certain embodiments, the neurostimulation lead 106 includes one or more anchors 130. In certain instances, the one or more anchors 130 are configured to secure the neurostimulation lead 106 to a portion of the spinal column (see, e.g., FIG. 2A illustrating a cross-section of the spinal column) including, for example, a vertebra and/or another structure of the spinal column and/or to a soft tissue structure to prevent migration and/or movement of the neurostimulation lead 106. For example, the one or more anchors 130 are configured to secure the neurostimulation lead 106 to the dura, the ligamentum flavum, or other soft tissue structure(s) to prevent migration and/or movement of the neurostimulation lead 106. In some aspects, the one or more anchors 130 are formed in the shape of barbs to couple to a vertebra and/or another solid structure of the spinal column. In certain embodiments, the one or more anchors 130 are formed from a shape memory material, for example, NiTi. In some examples, the one or more anchors 130 protrude from a top of the neurostimulation lead 106. Additionally, or alternatively, the one or more anchors 130 protrude from another portion of the neurostimulation lead 106, for example, the sides and/or bottom. In certain embodiments, the one or more anchors 130 may be formed of a material that encourages tissue ingrowth into the one or more anchors 130. In addition to or alternatively to the one or more anchors 130, the neurostimulation lead 106 can be comprised a different materials, some or all of the materials may encourage tissue ingrowth/attachment to a portion of the spinal column and some of the materials may inhibit tissue ingrowth/attachment. For example, materials that can encourage tissue ingrowth/attachment can be materials having open high-porosity microstructures and materials that inhibit tissue ingrowth/attachment can be materials having closed low-porosity microstructures. Additional details describing such materials may be found in U.S. Pat. No. 7,736,576 entitled, "SURFACE MODIFIED EXPANDED POLYTETRAFLUOROETHYLENE DEVICES AND METHODS OF PRODUCING THE SAME," U.S. patent application Ser. No. 15/183,897 entitled, "ASYMMETRIC POLYTETRAFLUOROETHYLENE COMPOSITE HAVING A MACRO-TEXTURED SURFACE AND METHOD FOR MAKING THE SAME," the entire disclosure of which are hereby incorporated by reference for all purposes in their entireties.

FIGS. 3A-3M are side views and distal-end views of an example delivery device and a neurostimulation lead 208 being arranged within the delivery device (FIGS. 3A-3G) and then transitioning from a collapsed delivery configuration to an expanded deployed configuration (FIGS. 3H-3M), in accordance with at least some embodiments of the present disclosure. In certain aspects, the embodiments disclosed in FIGS. 3H-3M can be performed in reverse from FIG. 3M to FIG. 3H to transition the neurostimulation lead 208 from the expanded deployed configuration to the collapsed delivery configuration. These diagrams are merely examples, which should not unduly limit the scope of the claims. One of ordinary skill in the art would recognize many variations, alternatives, and modifications.

FIG. 3A illustrates an example neurostimulation lead 208 that can be arranged within a delivery device shown in FIG. 3B. In the illustrated embodiment, the neurostimulation lead 208 includes a paddle portion 208A connected lead wire 208B. In some embodiments, the neurostimulation lead 208 can have the same or similar characteristics as the neurostimulation lead 106 shown in FIGS. 1-2B.

According to certain embodiments, the body portion 214 of the neurostimulation lead 208 has a width 209 when the neurostimulation lead 208 is in an expanded deployed configuration that is greater than when the neurostimulation lead 208 is in a collapsed delivery configuration. Additionally, or alternatively, the body portion 214 of the neurostimulation lead 208 has a cross-sectional thickness 211 when the neurostimulation lead 208 is in an expanded deployed configuration that is less than when the neurostimulation lead 208 is in a collapsed delivery configuration, as shown by the comparison of FIG. 3A and FIG. 3D. According to certain embodiments, the width 209 and the cross-sectional thickness 211 can be defined the same as the width 107 and cross-sectional thickness 109 shown in FIGS. 2A and 2B. Additionally, or alternatively, in certain embodiments, the cross-sectional area of the neurostimulation lead 208 is smaller in the collapsed delivery configuration than in the expanded deployed configuration. Additionally, or alternatively, the body portion 214 of the neurostimulation lead 208 can be curved when the neurostimulation lead 208 is in the expanded deployed in the same or similar manner that the neurostimulation lead 106 is curved.

In certain embodiments, the delivery device includes a rod 202 with a slot 204 extending from an end of the rod 202 down the rod 202, as shown in FIG. 3B. In some embodiments, the slot 204 extends down approximately the middle of the rod 202. In certain instances, the slot 204 extends down approximately the middle of the rod 202 by a distance that is greater than or equal to a length 213 of the paddle portion 208A of the neurostimulation lead 208. In some embodiments, the length 213 of the paddle portion 208A of the neurostimulation lead 208 can be a distance extending along a longitudinal axis 215 of the neurostimulation lead 208 from a distal end 215 of the paddle portion 208A to a proximal end 217 of the paddle portion 208A. The neurostimulation lead 208 can then be positioned within the slot 204, as shown in FIG. 3C. After which, the rod 202 can be twisted in a clockwise or counterclockwise manner so that the neurostimulation lead 208 wraps around the rod 202, as shown in FIG. 3D.

In certain aspects, the delivery device includes a delivery sheath 206, as shown in FIG. 3E. The delivery sheath 206 can be arranged over the neurostimulation lead 208 and the rod 202 so that the delivery sheath 206 surrounds the neurostimulation lead 208 and the rod 202 to prevent the neurostimulation lead 208 from unintentionally unrolling during, for example, implantation of the neurostimulation lead 208. According to certain embodiments, the sheath 206 includes one or more slots 210 extending from an end of the sheath 206 down one or more sides of the sheath 206. In some embodiments, the neurostimulation lead 208 includes edges 212 that extend into the slots 210 of the delivery sheath 206, as shown in FIG. 3F. In some instances, the delivery device can include an external delivery sheath 213 that surrounds the delivery sheath 206 and the neurostimulation lead 208, as shown in FIG. 3G. In instances, the external delivery sheath 213 can enclose the edges 212 of the neurostimulation lead 208 during implantation of the neurostimulation lead 208 to prevent the edges 212 from protruding during implantation of the neurostimulation lead 208. The rod 202, delivery sheath 206, and the external delivery sheath 213 can be referred to herein as the delivery device.

According to certain aspects, the neurostimulation lead 208 and the delivery device 202, 206, 213 can be positioned percutaneously within a subject 108. Once the neurostimulation lead 208 and the delivery device 202, 206, 213 is positioned at an implantation site, e.g., in the epidural space 132 of the subject 108, the neurostimulation lead 208 can be deployed, as shown in FIGS. 3H-3M.

Figures 3H, 3I, 3J, 3K, 3L, 3M:
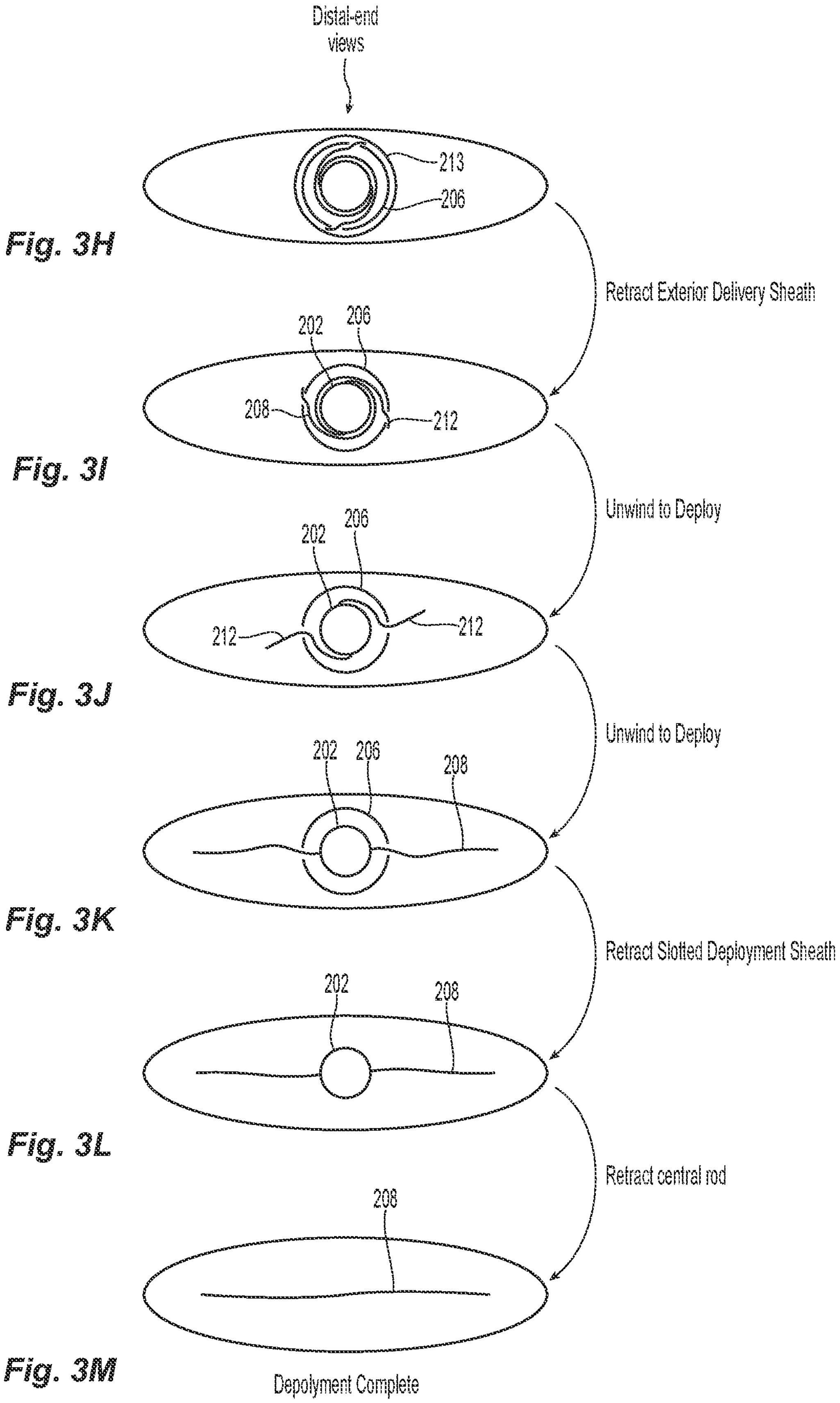

To transition the neurostimulation lead 208 from the collapsed delivery configuration shown in FIG. 3H to an expanded deployed configuration shown in FIG. 3M, the external delivery sheath 213 can be retracted, as shown by the transition from FIG. 3H to FIG. 3I. After which, in order to deploy the neurostimulation lead 208, the slots 210 in the delivery sheath 206 can first be aligned to lay in the coronal anatomical plane. The neurostimulation lead 208 and the rod 202 can then be twisted in a direction opposite the direction the neurostimulation lead 208 was twisted to wrap the neurostimulation lead 208 around the rod 202. For example, if the neurostimulation lead 208 was twisted in a clockwise direction to wrap the neurostimulation lead 208 around the rod 202, then the neurostimulation lead 208 can be twisted in a counterclockwise direction to initiate deployment of the neurostimulation lead 208. Conversely, if the neurostimulation lead 208 was twisted in a counterclockwise direction to wrap the neurostimulation lead 208 around the rod 202, then the rod 202 can be twisted in a clockwise direction to initiate deployment of the neurostimulation lead 208. As the neurostimulation lead 208 and the rod 202 are rotated to initiate deployment of the neurostimulation lead 208, as shown in FIGS. 3J, the edges 212 of the neurostimulation lead 208 protrude out of the slots 204 of the rod 202 until the neurostimulation lead 208 is fully expanded, as shown in FIG. 3K. In some embodiments, once the neurostimulation lead 208 is fully expanded, the delivery sheath 206 can be retracted, as shown in FIG. 3L. In some instances, the rod 202 can be retracted once the neurostimulation lead 208 is expanded to leave the neurostimulation lead 208 implanted within the epidural space 132 of the subject 108, as shown in FIG. 3M. The neurostimulation lead may include elements made from shape memory materials to assist in the deployment process. All components of the delivery device may be fabricated in such a way as to make them mechanically flexible to facilitate navigation of the delivery device to the deployment site.

Figure 5:
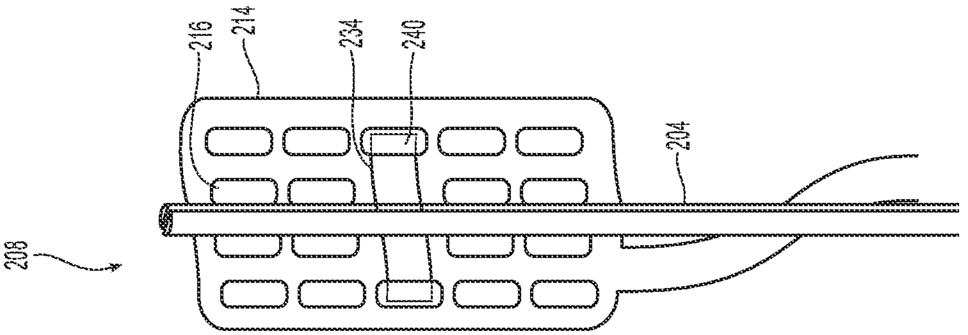
FIG. 4 is a side view of an example neurostimulation lead and FIG. 5 is an opposing side view of the example neurostimulation lead shown in FIG. 4, in accordance with at least some embodiments of the present disclosure.
Figure 4:
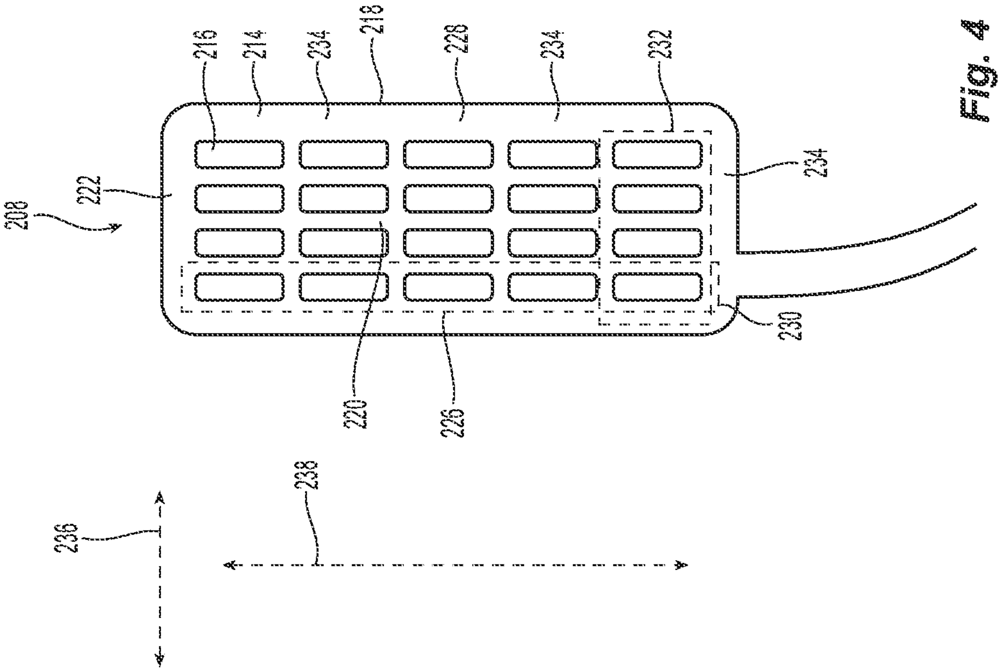

FIGS. 4 and 5 illustrate a side view of the neurostimulation lead 208 and an opposing side view of the neurostimulation lead 208, respectively. These diagrams are merely examples, which should not unduly limit the scope of the claims. One of ordinary skill in the art would recognize many variations, alternatives, and modifications.

According to certain embodiments, the neurostimulation lead includes a body portion 214. The body portion 214 can have a generally rectangular shape, as illustrated. Further, the body portion 214 can be arranged near the centerline of the spinal cord 133, the left and right sides of the spinal cord 133 and/or a portion of at least one dorsal root ganglion 134.

According to certain embodiments, the body portion 214 includes an array of electrodes 216 arranged on the body portion 214. The array of electrodes 216 can be coupled to an IPG (e.g., IPG 104) in order to receive electrical waveforms from the IPG and deliver the waveforms to stimulate locations on the spinal cord 133 and/or dorsal root ganglion 134.

According to certain embodiments, one or more electrodes of the array of electrodes 216 can be arranged near a perimeter 218 of the body portion 214. Additionally, or alternatively, one or more electrodes of the array of electrodes 216 can be arranged away from the perimeter 218 of the body portion 214 near, for example, a central portion 220 of the body portion 214. Additionally, or alternatively, one or more electrodes of the array of electrodes 216 can be arranged near a distal portion 222, a proximal portion 224, a left portion 226, and/or a right portion 228 of the body portion 214. In certain embodiments, one or more of the electrodes of the array of electrodes 216 can be arranged in one or more columns, for example, column 230. Additionally, or alternatively, one or more of the electrodes of the array of electrodes 216 can be arranged in one or more rows, for example, row 232. Each column 230 and/or row 232 can include multiple electrodes, as illustrated.

According to certain embodiments, due to the wide coverage area of the body portion 214 and/or the array of electrodes 216, the neurostimulation lead 208 can provide better stimulation and/or more accurate stimulation than a narrower neurostimulation lead. Further, the neurostimulation lead 208 can be implanted percutaneously due to the smaller profile of the neurostimulation lead 208 while the neurostimulation lead 208 is in the collapsed delivery configuration.

In certain embodiments, the neurostimulation lead 208 can be formed from and/or coated by a biocompatible material, such as PE, ePE, PTFE or ePTFE.

According to certain embodiments, the neurostimulation lead 208 includes a frame extending around a perimeter 218 constructed from a shape-memory material. In some instances, the frame is in a relaxed shape when the neurostimulation lead 208 is an in expanded deployed configuration. For example, NiTi may be used as the material of the frame (and any of the frames discussed herein) of the neurostimulation lead 208, but other materials such as, but not limited to, stainless steel, L605 steel, polymers, MP35N steel, Pyhnox, Elgiloy, or any other appropriate biocompatible material, and combinations thereof, can be used as the material of the frame.

Additionally, or alternatively, the neurostimulation lead 208 can include one or more stiffening bands 234. In certain instances, the one or more stiffening bands 234 can formed from a shape-memory material, such as NiTi. In certain instances, the one or more stiffening bands 234 can laterally extend (e.g., along the lateral direction 236) partially or fully across the neurostimulation lead 208. Additionally, or alternatively, the one or more stiffening bands 234 can longitudinally extend (e.g., along the longitudinal direction 238) partially or fully along the neurostimulation lead 208. Additionally, or alternatively, the one or more stiffening bands 234 can extend partially or fully across the neurostimulation lead 208 at a non-zero angle relative to the lateral direction 236 and/or the longitudinal direction 238. In some instances, the stiffening bands 234 can be retracted during the delivery of the neurostimulation lead 208 and can be extended during deployment of the neurostimulation lead 208. In certain instances, the one or more stiffening bands 234 can be inserted into one or more pockets 240 located on the back of the neurostimulation lead 208, as shown in FIG. 5. In some instances, the stiffening bands 234 can disengage from the pockets 240 and be retracted again after deployment of the neurostimulation lead 208.

According to certain embodiments, the neurostimulation lead 208 can additionally or alternatively be inflatable. By inflating the neurostimulation lead 208, the neurostimulation lead 208 can transition from a collapsed delivery configuration to an expanded deployed configuration. In certain aspects, the neurostimulation lead 208 can be pneumatically and/or hydraulically inflated using, for example, a hydrogel. In certain embodiments, the neurostimulation lead 208 can be deflated to transition the neurostimulation lead 208 from an expanded deployed configuration to the collapsed delivery configuration.

According to certain embodiments, the neurostimulation lead 208 can include a hardening agent so that when the neurostimulation lead 208 is in an expanded deployed configuration, the hardening agent can fix the neurostimulation lead 208 in the expanded deployed configuration to reduce the likelihood the neurostimulation lead 208 compresses and/or expands and/or migrates as the subject 108 moves, bends, twists, etc. In certain embodiments, the hardening agent can be injected into the neurostimulation lead 208.

According to certain embodiments, the neurostimulation lead 208 can include one or more anchors (e.g., anchors 130) to secure the neurostimulation lead 208 to a portion of the spinal column including, for example, to a vertebra and/or another structure of the spinal column or to a soft tissue structure to prevent migration and/or movement of the neurostimulation lead 208. According to certain embodiments, the neurostimulation lead 208 can include one or more anchors (e.g., anchors 130) to secure the neurostimulation lead 208 to the dura, the ligamentum flavum, or other soft tissue structure(s) to prevent migration and/or movement of the neurostimulation lead 208.

Figure 6B:
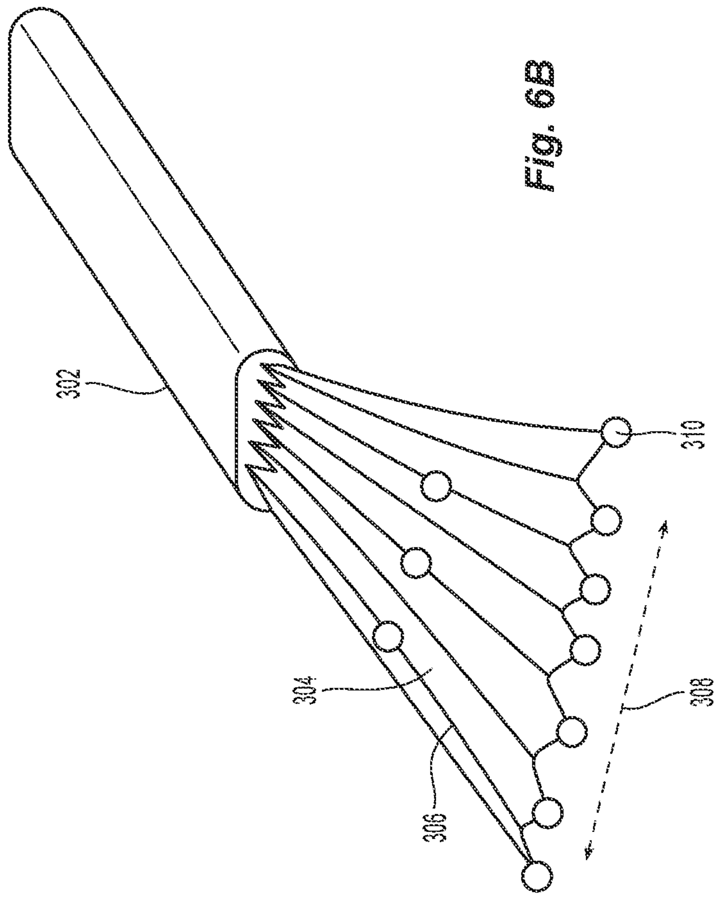
FIGS. 6A-6B are perspective views of an example neurostimulation lead, in accordance with at least some embodiments of the present disclosure.
Figure 6A:
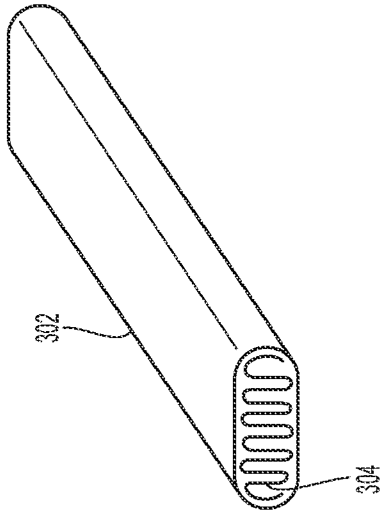

FIGS. 6A-6B are perspective views of an example neurostimulation lead, in accordance with at least some embodiments of the present disclosure. In particular, FIG. 6A illustrates a delivery device 302 including a neurostimulation lead 304 in a collapsed delivery configuration and FIG. 6B illustrates the delivery device 302 including the neurostimulation lead 304 in an expanded deployed configuration. According to certain embodiments, the neurostimulation lead 304 has a width that is greater when the neurostimulation lead 304 is in an expanded deployed configuration than when the neurostimulation lead 304 is in a collapsed delivery configuration. Additionally, or alternatively, the neurostimulation lead 304 has a cross-sectional thickness that is greater when the neurostimulation lead 304 is in a collapsed delivery configuration than when the neurostimulation lead 304 is in an expanded deployed configuration. According to certain embodiments, the width and the cross-sectional thickness of the neurostimulation lead 304 can be defined the same as the width 107 and cross-sectional thickness 109 shown in FIGS. 2A and 2B. Additionally, or alternatively, in certain embodiments, the cross-sectional area of the neurostimulation lead 304 is smaller in the collapsed delivery configuration than in the expanded deployed configuration. Additionally, or alternatively, the neurostimulation lead 304 can be curved when the neurostimulation lead 304 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 6A, the delivery device 302 is a tubular sheath that surrounds and confines the neurostimulation lead 304 to a collapsed delivery configuration to prevent the neurostimulation lead 304 from expanding earlier than desired. In some aspects, a neurostimulation lead 304 can be folded within the delivery device 302. For example, the neurostimulation lead 304 can include a plurality of folds 306 that, when compressed along the folds 306 in a lateral direction 308, the neurostimulation lead 304 collapses to the delivery configuration shown in FIG. 6A. According to certain aspects, the delivery device 302 and the neurostimulation lead 304 can be positioned percutaneously within a subject 108 while the neurostimulation lead 304 is in the collapsed delivery configuration. For example, the neurostimulation lead 304 can be arranged at an implantation site near the centerline of the spinal cord 133, the left and right sides of the spinal cord 133 and/or a portion of at least one dorsal root ganglion 134 within the epidural space 132. Once the neurostimulation lead 304 is positioned at an implantation site, the delivery device 302 can be removed (e.g., withdrawn) and the neurostimulation lead 304 can be deployed and expanded to the expanded deployed configuration shown in FIG. 6B. Due to the wide coverage area of the neurostimulation lead 304, the neurostimulation lead 304 can provide better stimulation and/or more accurate stimulation than a narrower neurostimulation lead due to being able to contact the left and right sides of the spinal cord 133 and/or at least one dorsal root ganglion 134. Further, the neurostimulation lead 304 can be implanted percutaneously (unlike some conventional embodiments that have a wider surface area) due to the smaller profile of the neurostimulation lead 304 while the neurostimulation lead 304 is in the collapsed delivery configuration. Additionally, or alternatively, the neurostimulation lead 304 can be transitioned from the expanded deployed configuration to the collapsed delivery configuration by arranging the device 302 over the neurostimulation lead 304.

According to certain embodiments, the neurostimulation lead 304 can have the same or similar characteristics as the neurostimulation lead 106 shown in FIGS. 1-2B and/or the neurostimulation lead 208 shown in FIGS. 3A-5. For example, the neurostimulation lead 304 can have an array of electrodes 310 that is the same as or similar to the array of electrodes 112 and/or the array of electrodes 216 that are arranged on the neurostimulation lead 304 and coupled to an IPG 104. Additionally, or alternatively, the neurostimulation lead 304 can be formed from and/or coated by a biocompatible material, such as PE, ePE, PTFE or ePTFE. Additionally, or alternatively, the neurostimulation lead 304 can include a frame formed from a shape-memory material, such as NiTi so that once the delivery device 302 is removed and no longer constrains the neurostimulation lead 304, the neurostimulation lead 304 expands to the expanded deployed configuration shown in FIG. 6B. As such, the frame is in a relaxed shape when the neurostimulation lead 304 is an in expanded deployed configuration. Additionally, or alternatively, the neurostimulation lead 304 can be inflatable to transition the neurostimulation lead 304 from a collapsed delivery configuration to an expanded deployed configuration. Additionally, or alternatively, the neurostimulation lead 304 can include a hardening agent so that when the neurostimulation lead 304 is in an expanded deployed configuration, a hardening agent can be added and/or applied to the neurostimulation lead 304 to fix the neurostimulation lead 304 in the expanded deployed configuration to reduce the likelihood the neurostimulation lead 304 compresses and/or expands and/or migrates as the subject 108 moves, bends, twists, etc. Additionally, or alternatively, the neurostimulation lead 304 can include one or more anchors (e.g., anchors 130) to secure the neurostimulation lead 304 to a portion of the spinal column (see, e.g., FIG. 2A illustrating a cross-section of the spinal column) including, for example, to a vertebra and/or another structure of the spinal column and/or to a soft tissue structure to prevent migration and/or movement of the neurostimulation lead 304. For example, the one or more anchors are configured to secure the neurostimulation lead 304 to the dura, the ligamentum flavum, or other soft tissue structure(s) to prevent migration and/or movement of the neurostimulation lead 304.

Figure 7B:
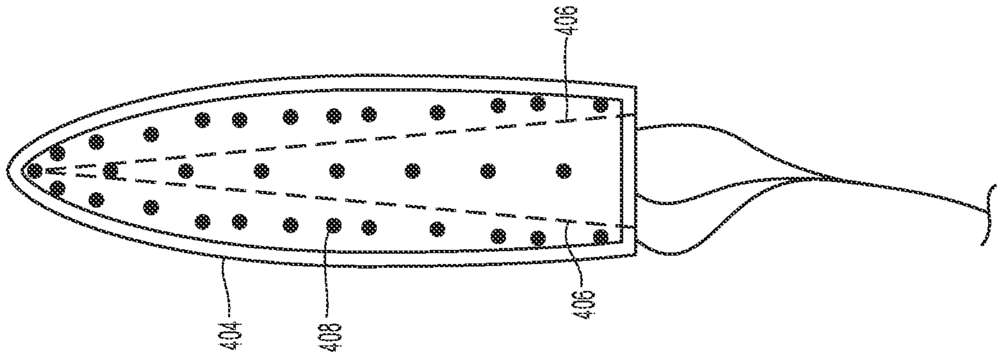
FIG. 7A is a distal-end view of an example neurostimulation lead and FIG. 7B is a side view of the example neurostimulation lead, in accordance with at least some embodiments of the present disclosure.
Figure 7A:
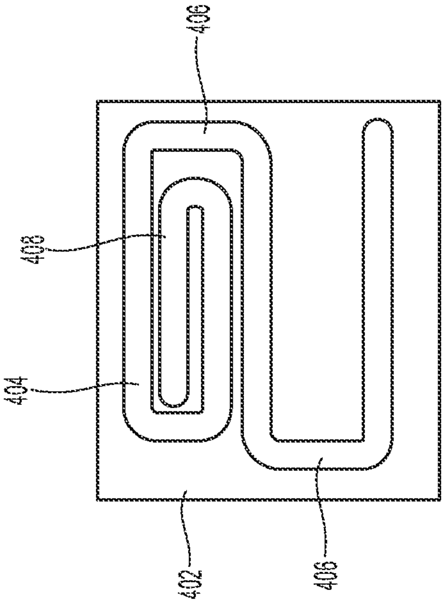

FIG. 7A is a distal-end view of an example neurostimulation lead and FIG. 7B is a side view of the example neurostimulation lead, in accordance with at least some embodiments of the present disclosure. In particular, FIG. 7A illustrates a delivery device 402 including a neurostimulation lead 404 in a collapsed delivery configuration and FIG. 7B illustrates the delivery device 402 including the neurostimulation lead 404 in an expanded deployed configuration. According to certain embodiments, the neurostimulation lead 404 has a width that is greater when the neurostimulation lead 404 is in an expanded deployed configuration than when the neurostimulation lead 404 is in a collapsed delivery configuration. Additionally, or alternatively, the neurostimulation lead 404 has a cross-sectional thickness that is greater when the neurostimulation lead 404 is in a collapsed delivery configuration than when the neurostimulation lead 404 is in an expanded deployed configuration. According to certain embodiments, the width and the cross-sectional thickness of the neurostimulation lead 404 can be defined the same as the width 107 and cross-sectional thickness 109 shown in FIGS. 2A and 2B. Additionally, or alternatively, in certain embodiments, the cross-sectional area of the neurostimulation lead 404 is smaller in the collapsed delivery configuration than in the expanded deployed configuration. Additionally, or alternatively, the neurostimulation lead 404 can be curved when the neurostimulation lead 404 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 7A, the delivery device 402 is a sheath that surrounds and confines the neurostimulation lead 404 to a collapsed delivery configuration to prevent the neurostimulation lead 404 from expanding earlier than desired. In some aspects, a neurostimulation lead 404 can be folded within the delivery device 402. For example, the neurostimulation lead 404 can include at least one fold 406 that, when compressed along the at least one fold 406, the neurostimulation lead 404 collapses to the delivery configuration shown in FIG. 7A. Additionally, or alternatively, the neurostimulation lead 404 may include one or more first portions that are thicker than a second portion of the neurostimulation lead 404. In these embodiments, the neurostimulation lead 404 can be arranged in a pattern such that the locations of at least one of the first portions do not longitudinally and/or laterally overlap with another first portion of the plurality of first portions when the lead is in its folded configuration. For example, the electrodes 408 on the neurostimulation lead 404 can be arranged in a pattern such that the locations of two electrodes do not longitudinally and/or laterally overlap when the lead is in its folded configuration. Stated another way, the electrodes 408 on the neurostimulation lead 404 can be arranged in a pattern such that the locations of two electrodes do not correspond to the same longitudinal and lateral position when the lead is in its folded configuration.

This can be done to maximize the packing density or to minimize the thickness and/or volume of the neurostimulation lead 404 in the collapsed delivery configuration. According to certain aspects, the delivery device 402 and the neurostimulation lead 404 can be positioned percutaneously within a subject 108 while the neurostimulation lead 404 is in the collapsed delivery configuration. For example, the neurostimulation lead 404 can be arranged at an implantation site near the centerline of the spinal cord 133, the left and right sides of the spinal cord 133 and/or a portion of at least one dorsal root ganglion 134 within the epidural space 132. Once the neurostimulation lead 404 is positioned at an implantation site, the delivery device 402 can be removed (e.g., withdrawn) and the neurostimulation lead 404 can be deployed and expanded to the expanded deployed configuration shown in FIG. 7B. Due to the wide coverage area of the neurostimulation lead 404, the neurostimulation lead 404 can provide better stimulation and/or more accurate stimulation than a narrower neurostimulation lead due to being able to contact the left and right sides of the spinal cord 133 and/or at least one dorsal root ganglion 134. Further, the neurostimulation lead 404 can be implanted percutaneously (unlike some conventional embodiments that have a wider surface area) due to the smaller profile of the neurostimulation lead 404 while the neurostimulation lead 404 is in the collapsed delivery configuration.

According to certain embodiments, the neurostimulation lead 404 can have the same or similar characteristics as the neurostimulation lead 106 shown in FIGS. 1-2B, the neurostimulation lead 208 shown in FIGS. 3A-5, and/or the neurostimulation lead 304 shown in FIGS. 6A-6B. For example, the neurostimulation lead 404 can have an array of electrodes 408 that is the same as or similar to the array of electrodes 112, the array of electrodes 216, and/or the array of electrodes 310. Additionally, or alternatively, the neurostimulation lead 404 can be formed from and/or coated by a biocompatible material, such as PE, ePE, PTFE or ePTFE. Additionally, or alternatively, the neurostimulation lead 404 can include a frame formed from a shape-memory material, such as NiTi so that once the delivery device 402 is removed and no longer constrains the neurostimulation lead 404, the neurostimulation lead 404 expands to the expanded deployed configuration shown in FIG. 7B. As such, the frame is in a relaxed shape when the neurostimulation lead 404 is an in expanded deployed configuration. Additionally, or alternatively, the neurostimulation lead 404 can be inflatable to transition the neurostimulation lead 404 from a collapsed delivery configuration to an expanded deployed configuration. In certain embodiments, the neurostimulation lead 404 can be deflated to transition the neurostimulation lead 404 from an expanded deployed configuration to the collapsed delivery configuration. Additionally, or alternatively, the neurostimulation lead 404 can include a hardening agent so that when the neurostimulation lead 404 is in an expanded deployed configuration, a hardening agent can be added and/or applied to the neurostimulation lead 404 to fix the neurostimulation lead 404 in the expanded deployed configuration to reduce the likelihood the neurostimulation lead 404 compresses and/or expands and/or migrates as the subject 108 moves, bends, twists, etc. Additionally, or alternatively, the neurostimulation lead 404 can include one or more anchors (e.g., anchors 130) to secure the neurostimulation lead 404 to a portion of the spinal column (see, e.g., FIG. 2A illustrating a cross-section of the spinal column) including, for example, to a vertebra and/or another structure of the spinal column and/or to a soft tissue structure to prevent migration and/or movement of the neurostimulation lead 404. For example, the one or more anchors are configured to secure the neurostimulation lead 404 to the dura, the ligamentum flavum, or other soft tissue structure(s) to prevent migration and/or movement of the neurostimulation lead 404. Additionally, or alternatively, the neurostimulation lead 404 can be transitioned from the expanded deployed configuration to the collapsed delivery configuration by arranging the device 402 over the neurostimulation lead 404.

Figure 8A:
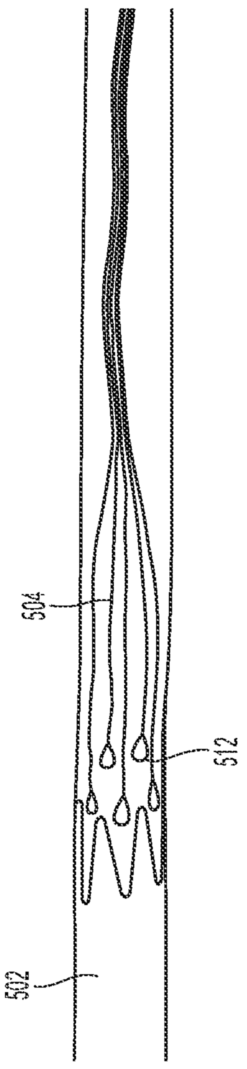
FIGS. 8A-8B are side views of an example neurostimulation lead and FIG. 8C is a perspective view of an example neurostimulation lead, in accordance with at least some embodiments of the present disclosure.
Figure 8B:
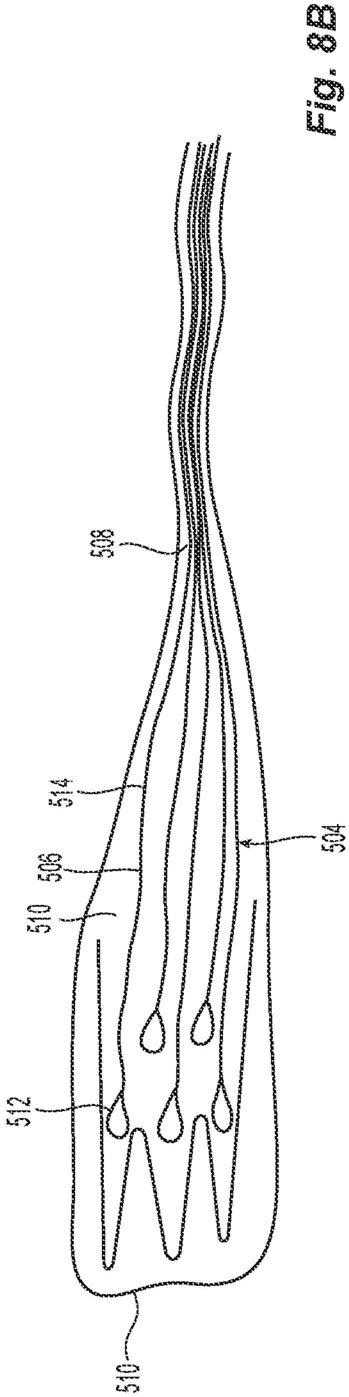
Figure 8C:
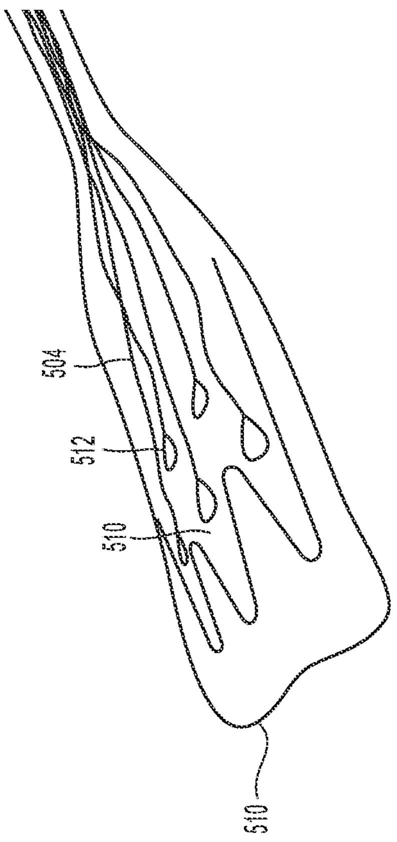

FIGS. 8A-8B are side views of an example neurostimulation lead and FIG. 8C is a perspective view of an example neurostimulation lead, in accordance with at least some embodiments of the present disclosure. In particular, FIG. 8A illustrates a delivery device 502 including a neurostimulation lead 504 in a collapsed delivery configuration and FIGS. 8B and 8C illustrate the neurostimulation lead 504 in an expanded deployed configuration. According to certain embodiments, the neurostimulation lead 504 has a greater width when the neurostimulation lead 504 is in an expanded deployed configuration than when the neurostimulation lead 504 is in a collapsed delivery configuration. Additionally, or alternatively, the neurostimulation lead 504 has a cross-sectional thickness that is greater when the neurostimulation lead 504 is in a collapsed delivery configuration than when the neurostimulation lead 504 is in an expanded deployed configuration. According to certain embodiments, the width and the cross-sectional thickness of the neurostimulation lead 504 can be defined the same as the width 107 and cross-sectional thickness 109 shown in FIGS. 2A and 2B.

Additionally, or alternatively, in certain embodiments, the cross-sectional area of the neurostimulation lead 504 is smaller in the collapsed delivery configuration than in the expanded deployed configuration. Additionally, or alternatively, the neurostimulation lead 504 can be curved when the neurostimulation lead 504 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 8A, the delivery device 502 is a sheath that surrounds and confines the neurostimulation lead 504 to a collapsed delivery configuration to prevent the neurostimulation lead 504 from expanding earlier than desired. According to certain aspects, the delivery device 502 and the neurostimulation lead 504 can be positioned percutaneously within a subject 108 while the neurostimulation lead 504 is in the collapsed delivery configuration. For example, the neurostimulation lead 504 can be arranged at an implantation site near the centerline of the spinal cord 133, the left and right sides of the spinal cord 133 and/or a portion of at least one dorsal root ganglion 134 within the epidural space 132. Once the neurostimulation lead 504 is positioned at an implantation site, the delivery device 502 can be removed (e.g., withdrawn) and the neurostimulation lead 504 can be deployed and expanded to the expanded deployed configuration shown in FIGS. 8B and 8C. Due to the wide coverage area of the neurostimulation lead 504, the neurostimulation lead 504 can provide better stimulation and/or more accurate stimulation than a narrower neurostimulation lead due to being able to contact the left and right sides of the spinal cord 133 and/or at least one dorsal root ganglion 134. Further, the neurostimulation lead 504 can be implanted percutaneously (unlike some conventional embodiments that have a wider surface area) due to the smaller profile of the neurostimulation lead 504 while the neurostimulation lead 504 is in the collapsed delivery configuration. Additionally, or alternatively, the neurostimulation lead 504 can be transitioned from the expanded deployed configuration to the collapsed delivery configuration by arranging the device 502 over the neurostimulation lead 504.

According to certain embodiments, the neurostimulation lead 504 can include a frame including multiple legs 506 extending from a proximal portion 508. In certain instances, the legs 506 can be coated, covered, and/or wrapped with a protective material 510, for example, High Strength Toughened Fluoropolymer (HSTF). Additionally, or alternatively, the neurostimulation lead 504 can include an array of electrodes 512. In certain embodiments, an electrode of the array of electrodes 512 can be included at the end of each leg 506. Additionally, or alternatively, one or more electrodes of the array of electrodes 512 can be arranged at intermediate positions 514 along one or more of the legs 506.

According to certain embodiments, the neurostimulation lead 504 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, and/or the neurostimulation lead 404 shown in FIGS. 7A-7B. For example, as set forth above, the neurostimulation lead 504 can have an array of electrodes 512 that is the same as or similar to the array of electrodes 112, the array of electrodes 216, the array of electrodes 310, and/or the array of electrodes 408. Additionally, or alternatively, the neurostimulation lead 504 can be formed from and/or coated by a biocompatible material, such as PE, ePE, PTFE or ePTFE. Additionally, or alternatively, the neurostimulation lead 504 can include a frame made from a shape-memory material, such as NiTi so that once the delivery device 502 is removed and no longer constrains the neurostimulation lead 504, the neurostimulation lead 504 expands to the expanded deployed configuration shown in FIGS. 8B and 8C. As such, the frame is in a relaxed shape when the neurostimulation lead 504 is an in expanded deployed configuration. Additionally, or alternatively, the neurostimulation lead 504 can include a hardening agent so that when the neurostimulation lead 504 is in an expanded deployed configuration, a hardening agent can be added and/or applied to the neurostimulation lead 504 to fix the neurostimulation lead 504 in the expanded deployed configuration to reduce the likelihood the neurostimulation lead 504 compresses and/or expands and/or migrates as the subject 108 moves, bends, twists, etc. Additionally, or alternatively, the neurostimulation lead 504 can include one or more anchors (e.g., anchors 130) to secure the neurostimulation lead 504 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 504. For example, the one or more anchors are configured to secure the neurostimulation lead 504 to the dura, the ligamentum flavum, or other soft tissue structure(s) to prevent migration and/or movement of the neurostimulation lead 504.

Figure 9:
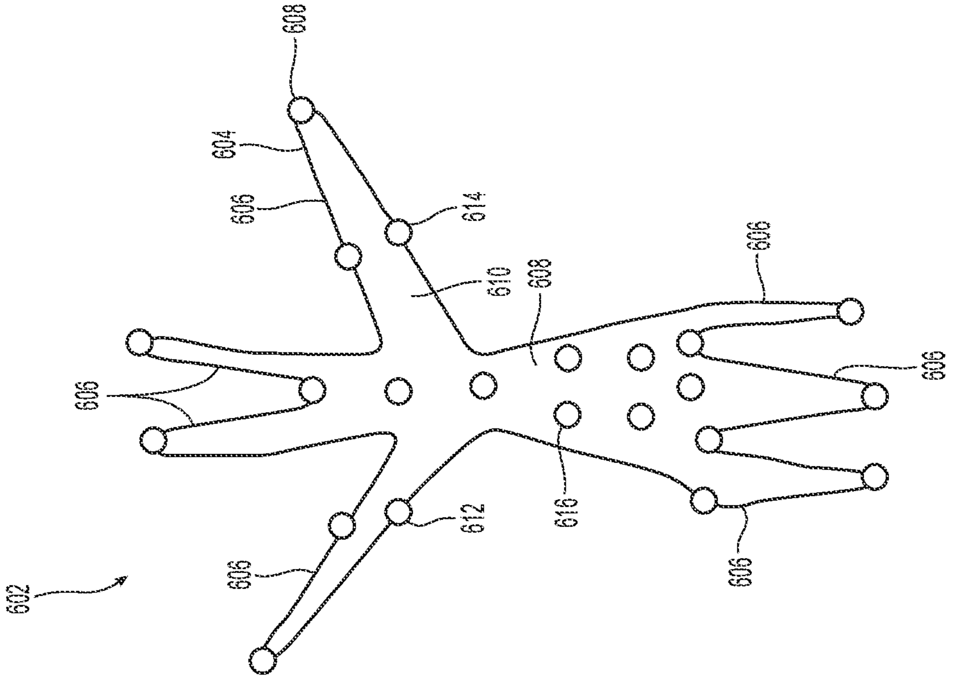
FIG. 9 is a side view of a neurostimulation lead, in accordance with at least some embodiments of the present disclosure.

FIG. 9 is a side view of a neurostimulation lead 602, in accordance with at least some embodiments of the present disclosure. According to certain embodiments, the neurostimulation lead 602 has a width that is greater when the neurostimulation lead 602 is in an expanded deployed configuration (as shown) than when the neurostimulation lead 602 is in a collapsed delivery configuration. Additionally, or alternatively, the neurostimulation lead 602 has a cross-sectional thickness that is greater when the neurostimulation lead 602 is in a collapsed delivery configuration than when the neurostimulation lead 602 is in an expanded deployed configuration. According to certain embodiments, the width and the cross-sectional thickness of the neurostimulation lead 602 can be defined the same as the width 107 and cross-sectional thickness 109 shown in FIGS. 2A and 2B. Additionally, or alternatively, in certain embodiments, the cross-sectional area of the neurostimulation lead 602 is smaller in the collapsed delivery configuration than in the expanded deployed configuration. Additionally, or alternatively, the neurostimulation lead 602 can be curved when the neurostimulation lead 602 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

According to certain embodiments, the neurostimulation lead 602 can be inserted into a delivery sheath (not shown) in order to collapse the neurostimulation lead 602 to a collapsed delivery configuration to prevent the neurostimulation lead 602 from expanding earlier than desired. According to certain aspects, a delivery device and the neurostimulation lead 602 can be positioned percutaneously within a subject 108 while the neurostimulation lead 602 is in the collapsed delivery configuration. For example, the neurostimulation lead 602 can be arranged at an implantation site near the centerline of the spinal cord 133, the left and right sides of the spinal cord 133 and/or a portion of at least one dorsal root ganglion 134 within the epidural space 132. Once the neurostimulation lead 602 is positioned at an implantation site, the delivery device can be removed (e.g., withdrawn) and the neurostimulation lead 602 can be deployed and expanded to the expanded deployed configuration as shown in FIG. 9. Due to the wide coverage area of the neurostimulation lead 602, the neurostimulation lead 602 can provide better stimulation and/or more accurate stimulation than a narrower neurostimulation lead due to being able to contact the left and right sides of the spinal cord 133 and/or at least one dorsal root ganglion 134. Further, the neurostimulation lead 602 can be implanted percutaneously (unlike some conventional embodiments that have a wider surface area) due to the smaller profile of the neurostimulation lead 602 while the neurostimulation lead 602 is in the collapsed delivery configuration.

According to certain embodiments, the neurostimulation lead 602 can include a frame 604 including multiple legs 606 extending away from a central portion 608. In certain instances, the frame 604 and legs 606 can be coated, covered, and/or wrapped with a protective material 610, for example, HSTF. Additionally, or alternatively, the neurostimulation lead 602 can include an array of electrodes 612. In certain embodiments, an electrode of the array of electrodes 612 can be included at one or more ends of each leg 606. Additionally, or alternatively, one or more electrodes of the array of electrodes 612 can be arranged along a periphery of the frame (e.g., at an intermediate position 614 along one or more of the legs 606) and/or at one or more locations 616 interior to the frame 604.

According to certain embodiments, the neurostimulation lead 602 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, and/or the neurostimulation lead 504 shown in FIGS. 8A-8C. For example, as set forth above, the neurostimulation lead 602 can have an array of electrodes 608 that is the same as or similar to the array of electrodes 112, the array of electrodes 216, the array of electrodes 310, the array of electrodes 408, and/or the array of electrodes 512. Additionally, or alternatively, the neurostimulation lead 602 can be formed from and/or coated by a biocompatible material, such as PE, ePE, PTFE or ePTFE. Additionally, or alternatively, the neurostimulation lead 602 can incorporate a frame formed from a shape-memory material, such as NiTi so that once the delivery device is removed and no longer constrains the neurostimulation lead 602, the neurostimulation lead 602 expands to the expanded deployed configuration shown in FIG. 9. As such, the frame is in a relaxed shape when the neurostimulation lead 602 is an in expanded deployed configuration. Additionally, or alternatively, the neurostimulation lead 602 can include a hardening agent so that when the neurostimulation lead 602 is in an expanded deployed configuration, a hardening agent can be added and/or applied to the neurostimulation lead 602 to fix the neurostimulation lead 602 in the expanded deployed configuration to reduce the likelihood the neurostimulation lead 602 compresses and/or expands and/or migrates as the subject 108 moves, bends, twists, etc. Additionally, or alternatively, the neurostimulation lead 602 can include one or more anchors (e.g., anchors 130) to secure the neurostimulation lead 602 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 602. For example, the one or more anchors are configured to secure the neurostimulation lead 602 to the dura, the ligamentum flavum, or other soft tissue structure(s) to prevent migration and/or movement of the neurostimulation lead 602.

Figure 10:
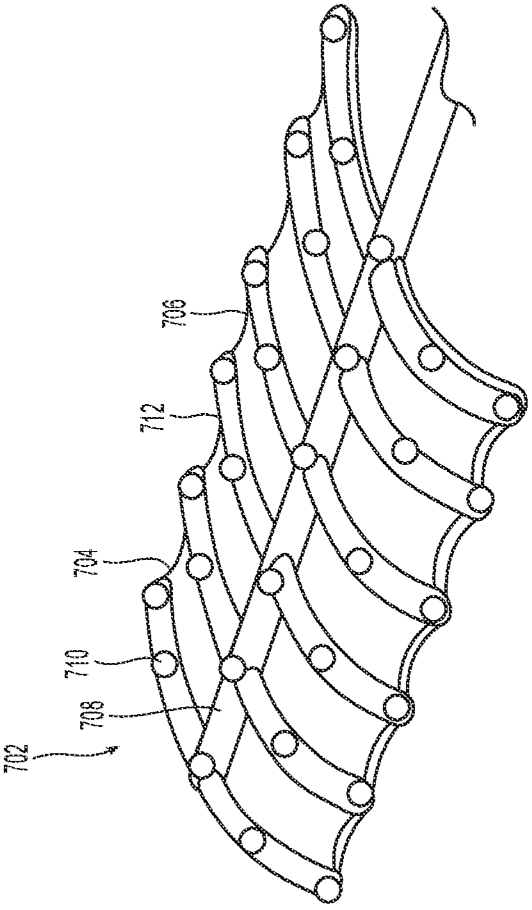
FIG. 10 is a perspective view of a frame for a neurostimulation lead.
Figure 11:
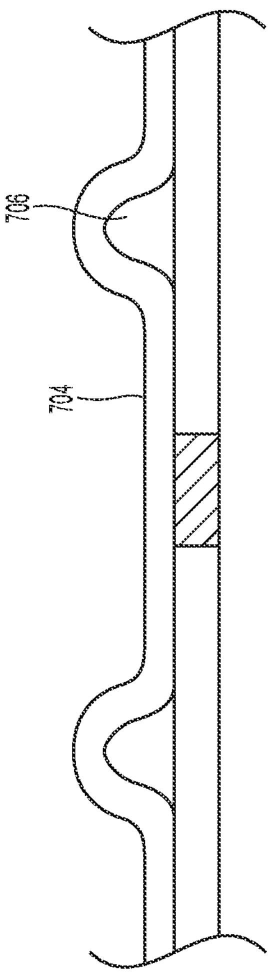
FIG. 11 is a cross-sectional view of a portion of the neurostimulation lead shown in FIG. 10, in accordance with at least some embodiments of the present disclosure.

FIG. 10 is a perspective view of a frame for a neurostimulation lead 702 and FIG. 11 is a cross-sectional view of a portion of the neurostimulation lead 702 shown in FIG. 10, in accordance with at least some embodiments of the present disclosure. According to certain embodiments, the neurostimulation lead 702 has a width that is greater when the neurostimulation lead 702 is in an expanded deployed configuration (as shown in FIG. 10) than when the neurostimulation lead 702 is in a collapsed delivery configuration. Additionally, or alternatively, the neurostimulation lead 702 has a cross-sectional thickness that is greater when the neurostimulation lead 702 is in a collapsed delivery configuration than when the neurostimulation lead 702 is in an expanded deployed configuration. According to certain embodiments, the width and the cross-sectional thickness of the neurostimulation lead 702 can be defined the same as the width 107 and cross-sectional thickness 109 shown in FIGS. 2A and 2B. Additionally, or alternatively, in certain embodiments, the cross-sectional area of the neurostimulation lead 702 is smaller in the collapsed delivery configuration than in the expanded deployed configuration. Additionally, or alternatively, the neurostimulation lead 702 can be curved when the neurostimulation lead 702 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

According to certain embodiments, the neurostimulation lead 702 can be inserted into a delivery sheath (not shown) in order to collapse the neurostimulation lead 702 to a collapsed delivery configuration to prevent the neurostimulation lead 702 from expanding earlier than desired. According to certain aspects, a delivery device and the neurostimulation lead 702 can be positioned percutaneously within a subject 108 while the neurostimulation lead 702 is in the collapsed delivery configuration. For example, the neurostimulation lead 702 can be arranged at an implantation site near the centerline of the spinal cord 133, the left and right sides of the spinal cord 133 and/or a portion of at least one dorsal root ganglion 134 within the epidural space 132. Once the neurostimulation lead 702 is positioned at an implantation site, the delivery device can be removed (e.g., withdrawn) and the neurostimulation lead 702 can be deployed and expanded to the expanded deployed configuration as shown in FIG. 10. Due to the wide coverage area of the neurostimulation lead 702, the neurostimulation lead 702 can provide better stimulation and/or more accurate stimulation than a narrower neurostimulation lead due to being able to contact the left and right sides of the spinal cord 133 and/or at least one dorsal root ganglion 134. Further, the neurostimulation lead 702 can be implanted percutaneously (unlike some conventional embodiments that have a wider surface area) due to the smaller profile of the neurostimulation lead 702 while the neurostimulation lead 702 is in the collapsed delivery configuration.

According to certain embodiments, the neurostimulation lead 702 can include an inflatable frame 704 including multiple channels and/or side supports 706 extending away from a central channel and/or central spine 708. In certain instances, the neurostimulation lead 702 may be referred to herein as having a fishbone shape and/or fishbone spinal array. In certain instances, the neurostimulation lead 702 can include an array of electrodes 710. In certain embodiments, an electrode of the array of electrodes 710 can be included at the end of each channel and/or side support 706. Additionally, or alternatively, one or more electrodes of the array of electrodes 710 can be arranged at intermediate positions 712 along one or more of the channels and/or side supports 706. In certain embodiments, the neurostimulation lead 702 can be deflated to transition the neurostimulation lead 702 from an expanded deployed configuration to the collapsed delivery configuration. According to certain embodiments, the neurostimulation lead 702 includes the features disclosed herein but is not inflatable and is comprised of a shape-memory material that facilitates transition of the neurostimulation lead 702 from its collapsed delivery configuration to the expanded deployed configuration.

According to certain embodiments, the neurostimulation lead 702 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, the neurostimulation lead 504 shown in FIGS. 8A-8C, and/or the neurostimulation lead 602 shown in FIG. 9. For example, as set forth above, the neurostimulation lead 702 can have an array of electrodes 710 that is the same as or similar to the array of electrodes 112, the array of electrodes 216, the array of electrodes 310, the array of electrodes 408, the array of electrodes 512 and/or the array of electrodes 608. Additionally, or alternatively, the neurostimulation lead 702 can include a hardening agent so that when the neurostimulation lead 702 is in an expanded deployed configuration, a hardening agent can be added and/or applied to the neurostimulation lead 702 to fix the neurostimulation lead 702 in the expanded deployed configuration to reduce the likelihood the neurostimulation lead 702 compresses and/or expands and/or migrates as the subject 108 moves, bends, twists, etc. Additionally, or alternatively, the neurostimulation lead 702 can include one or more anchors (e.g., anchors 130) to secure the neurostimulation lead 702 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 702. For example, the one or more anchors are configured to secure the neurostimulation lead 702 to the dura, the ligamentum flavum, or other soft tissue structure(s) to prevent migration and/or movement of the neurostimulation lead 702.

Figure 12:
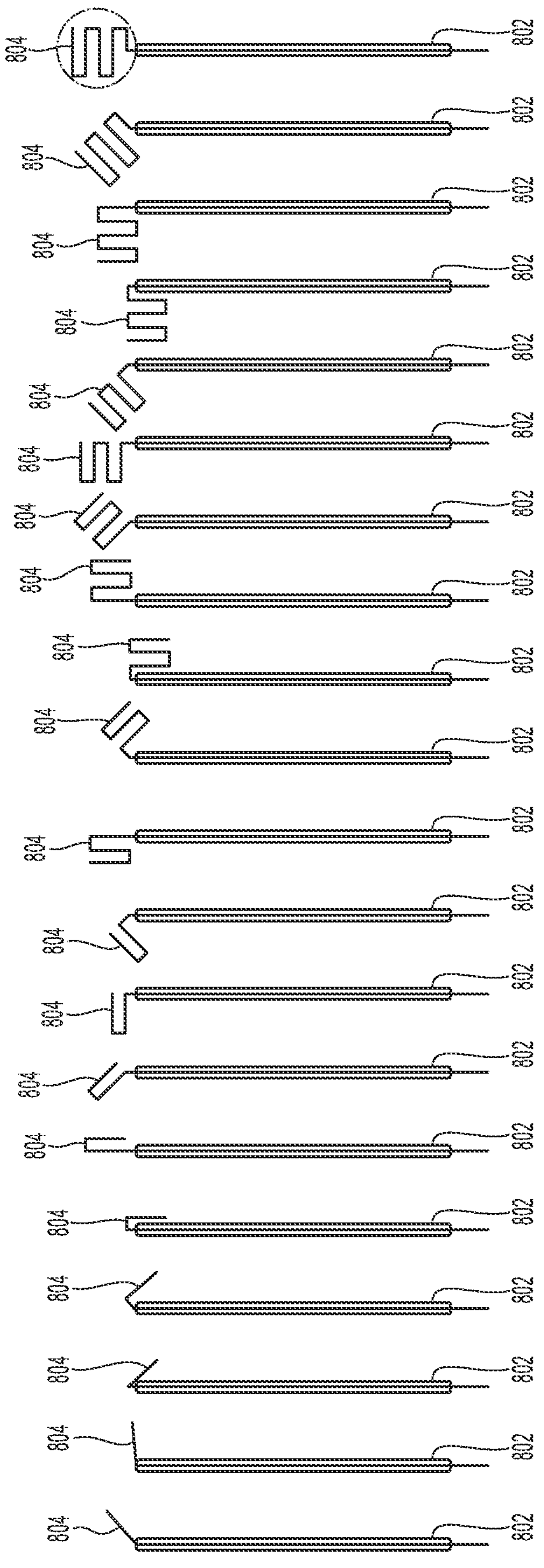
FIG. 12 are side views of a neurostimulation lead transitioning from a collapsed delivery state to an expanded deployed state and FIG. 13 is an expanded view of a portion of the neurostimulation lead shown in FIG. 12, in accordance with at least some embodiments of the present disclosure.
Figure 13:
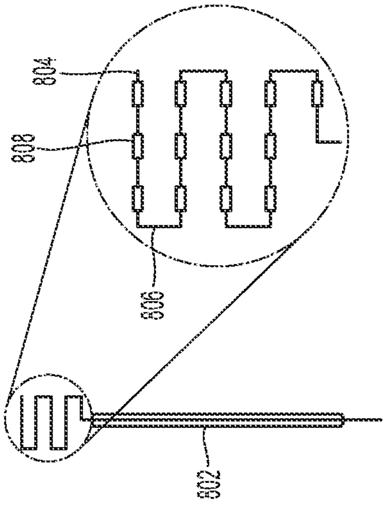

FIG. 12 are side views of a neurostimulation lead transitioning from a collapsed delivery state to an expanded deployed state and FIG. 13 is an expanded view of a portion of the neurostimulation lead shown in FIG. 11, in accordance with at least some embodiments of the present disclosure. In particular, FIG. 12 illustrates a delivery device 802 including a neurostimulation lead 804 transitioning from a collapsed delivery configuration (left side of FIG. 12) to an expanded deployed configuration (right side of FIG. 12 and FIG. 13). Additionally, or alternatively, the neurostimulation lead 804 can be transitioned from the expanded deployed configuration to the collapsed delivery configuration by arranging the device 802 over the neurostimulation lead 804. In certain aspects, the neurostimulation lead 804 has a serpentine shape (e.g., sinusoidal shape). According to certain embodiments, the neurostimulation lead 804 has a width that is greater when the neurostimulation lead 804 is in an expanded deployed configuration (right side of FIG. 12 and FIG. 13) than when the neurostimulation lead 804 is in a collapsed delivery configuration (left side of FIG. 12). Additionally, or alternatively, the neurostimulation lead 804 has a cross-sectional thickness that is greater when the neurostimulation lead 804 is in a collapsed delivery configuration than when the neurostimulation lead 804 is in an expanded deployed configuration. According to certain embodiments, the width and the cross-sectional thickness of the neurostimulation lead 804 can be defined the same as the width 107 and cross-sectional thickness 109 shown in FIGS. 2A and 2B. Additionally, or alternatively, in certain embodiments, the cross-sectional area of the neurostimulation lead 804 is smaller in the collapsed delivery configuration than in the expanded deployed configuration. Additionally, or alternatively, the neurostimulation lead 804 can be curved when the neurostimulation lead 304 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 12, the delivery device 802 is a tubular sheath that surrounds and confines the neurostimulation lead 804 to a collapsed delivery configuration to prevent the neurostimulation lead 804 from expanding earlier than desired. In some aspects, a neurostimulation lead 804 can include bends 806 that are unbent and/or smoothed when the neurostimulation lead 804 is within the delivery device 802, as shown on the left side of FIG. 12 and FIG. 13. Then, as the delivery device 802 is removed, the neurostimulation lead 804 bends along bends 806 to assume the expanded deployed configuration shown in the right side of FIG. 12 and FIG. 13.

According to certain aspects, the delivery device 802 and the neurostimulation lead 804 can be positioned percutaneously within a subject 108 while the neurostimulation lead 804 is in the collapsed delivery configuration. For example, the neurostimulation lead 804 can be arranged at an implantation site near the centerline of the spinal cord 133, the left and right sides of the spinal cord 133 and/or a portion of at least one dorsal root ganglion 134 within the epidural space 132. Once the neurostimulation lead 804 is positioned at an implantation site, the delivery device 802 can be removed (e.g., withdrawn) and the neurostimulation lead 804 can be deployed and expanded to the expanded deployed configuration shown on the right side of FIG. 12 and FIG. 13. Due to the wide coverage area of the neurostimulation lead 804, the neurostimulation lead 804 can provide better stimulation and/or more accurate stimulation than a narrower neurostimulation lead due to being able to contact the left and right sides of the spinal cord 133 and/or at least one dorsal root ganglion 134. Further, the neurostimulation lead 804 can be implanted percutaneously (unlike some conventional embodiments that have a wider surface area) due to the smaller profile of the neurostimulation lead 804 while the neurostimulation lead 804 is in the collapsed delivery configuration.

According to certain embodiments, the neurostimulation lead 804 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, the neurostimulation lead 504 shown in FIGS. 8A-8C, the neurostimulation lead 602 shown in FIG. 9, and/or the neurostimulation lead 702 shown in FIGS. 10 and 11. For example, the neurostimulation lead 804 can have an array of electrodes 808 that is the same as or similar to the array of electrodes 112, the array of electrodes 216, the array of electrodes 310, the array of electrodes 408, the array of electrodes 512, the array of electrodes 608, and/or the array of electrodes 710. Additionally, or alternatively, the neurostimulation lead 804 can be formed from and/or coated by a biocompatible material, such as PE, ePE, PTFE or ePTFE. Additionally, or alternatively, the neurostimulation lead 804 can be formed from a shape-memory material, such as NiTi so that once the delivery device 802 is removed and no longer constrains the neurostimulation lead 804, the neurostimulation lead 804 expands to the expanded deployed configuration shown on the right side of FIG. 12 and FIG. 13. As such, the neurostimulation lead 804 is in a relaxed shape when the neurostimulation lead 804 is an in expanded deployed configuration. Additionally, or alternatively, the neurostimulation lead 804 can include a hardening agent so that when the neurostimulation lead 804 is in an expanded deployed configuration, a hardening agent can be added and/or applied to the neurostimulation lead 804 to fix the neurostimulation lead 804 in the expanded deployed configuration to reduce the likelihood the neurostimulation lead 804 compresses and/or expands and/or migrates as the subject 108 moves, bends, twists, etc. Additionally, or alternatively, the neurostimulation lead 804 can include one or more anchors (e.g., anchors 130) to secure the neurostimulation lead 804 to a portion of the spinal column (see, e.g., FIG. 2A illustrating a cross-section of the spinal column) including, for example, to a vertebra and/or another solid structure and/or to a soft tissue structure of the spinal column to prevent migration and/or movement of the neurostimulation lead 804. For example, the one or more anchors are configured to secure the neurostimulation lead 804 to the dura, the ligamentum flavum, or other soft tissue structure(s) to prevent migration and/or movement of the neurostimulation lead 804.

Figure 14:
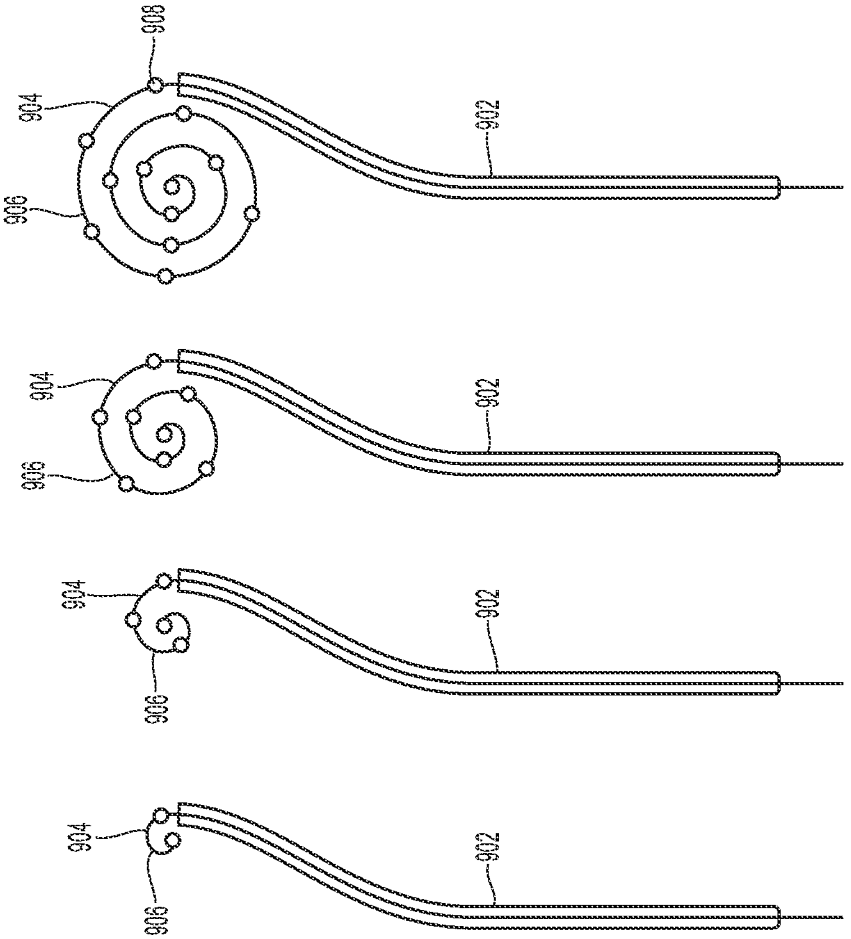
FIG. 14 are side views of a neurostimulation lead transitioning from a collapsed delivery state to an expanded deployed state, in accordance with embodiments of the present disclosure.

FIG. 14 are side views of a neurostimulation lead transitioning from a collapsed delivery state to an expanded deployed state, in accordance with embodiments of the present disclosure. In particular, FIG. 14 illustrates a delivery device 902 including a neurostimulation lead 904 transitioning from a collapsed delivery configuration (left side of FIG. 14) to an expanded deployed configuration (right side of FIG. 14). Additionally, or alternatively, the neurostimulation lead 904 can be transitioned from the expanded deployed configuration to the collapsed delivery configuration by arranging the device 902 over the neurostimulation lead 904.

In certain aspects, the neurostimulation lead 904 has a coil shape. According to certain embodiments, the neurostimulation lead 904 has a width that is greater when the neurostimulation lead 904 is in an expanded deployed configuration (right side of FIG. 14) than when the neurostimulation lead 904 is in a collapsed delivery configuration (left side of FIG. 14). Additionally, or alternatively, the neurostimulation lead 904 has a cross-sectional thickness that is greater when the neurostimulation lead 904 is in a collapsed delivery configuration than when the neurostimulation lead 904 is in an expanded deployed configuration. According to certain embodiments, the width and the cross-sectional thickness of the neurostimulation lead 904 can be defined the same as the width 107 and cross-sectional thickness 109 shown in FIGS. 2A and 2B. Additionally, or alternatively, in certain embodiments, the cross-sectional area of the neurostimulation lead 904 is smaller in the collapsed delivery configuration than in the expanded deployed configuration. Additionally, or alternatively, the neurostimulation lead 904 can be curved when the neurostimulation lead 904 is in the expanded deployed in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 14, the delivery device 902 is a tubular sheath that surrounds and confines the neurostimulation lead 904 to a collapsed delivery configuration to prevent the neurostimulation lead 904 from expanding earlier than desired. In some aspects, a neurostimulation lead 904 can include a curvature 906 that is smoothed when the neurostimulation lead 904 is within the delivery device 902, as shown on the left side of FIG. 14. Then, as the neurostimulation lead 904 is advanced through delivery device 902, the neurostimulation lead 904 curves along curvature 906 to assume the expanded deployed configuration shown in the right side of FIG. 14. After the expanded deployed configuration is achieved, the delivery device 902 may be removed.

According to certain aspects, the delivery device 902 and the neurostimulation lead 904 can be positioned percutaneously within a subject 108 while the neurostimulation lead 904 is in the collapsed delivery configuration. For example, the neurostimulation lead 904 can be arranged at an implantation site near the centerline of the spinal cord 133, the left and right sides of the spinal cord 133 and/or a portion of at least one dorsal root ganglion 134 within the epidural space 132. Once the neurostimulation lead 904 is positioned at an implantation site, the delivery device 902 can be removed (e.g., withdrawn) and the neurostimulation lead 904 can be deployed and expanded to the expanded deployed configuration shown on the right side of FIG. 14. Due to the wide coverage area of the neurostimulation lead 904, the neurostimulation lead 904 can provide better stimulation and/or more accurate stimulation than a narrower neurostimulation lead due to being able to contact the left and right sides of the spinal cord 133 and/or at least one dorsal root ganglion 134. Further, the neurostimulation lead 904 can be implanted percutaneously (unlike some conventional embodiments that have a wider surface area) due to the smaller profile of the neurostimulation lead 904 while the neurostimulation lead 904 is in the collapsed delivery configuration.

According to certain embodiments, the neurostimulation lead 904 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, the neurostimulation lead 504 shown in FIGS. 8A-8C, the neurostimulation lead 602 shown in FIG. 9, the neurostimulation lead 702 shown in FIGS. 10 and 11 and/or the neurostimulation lead 804 shown in FIGS. 12 and 13. For example, the neurostimulation lead 904 can have an array of electrodes 908 that is the same as or similar to the array of electrodes 112, the array of electrodes 216, the array of electrodes 310, the array of electrodes 408, the array of electrodes 512, the array of electrodes 608, the array of electrodes 710, and/or the array of electrodes 808. Additionally, or alternatively, the neurostimulation lead 904 can be formed from and/or coated by a biocompatible material, such as PE, ePE, PTFE or ePTFE. Additionally, or alternatively, the neurostimulation lead 904 can be formed in part from a shape-memory material, such as NiTi so that once the delivery device 902 is removed and no longer constrains the neurostimulation lead 904, the neurostimulation lead 904 expands to the expanded deployed configuration shown on the right side of FIG. 14. As such, the neurostimulation lead 904 is in a relaxed shape when the neurostimulation lead 904 is an in expanded deployed configuration. Additionally, or alternatively, the neurostimulation lead 904 can include a hardening agent so that when the neurostimulation lead 904 is in an expanded deployed configuration, a hardening agent can be added and/or applied to the neurostimulation lead 904 to fix the neurostimulation lead 904 in the expanded deployed configuration to reduce the likelihood the neurostimulation lead 904 compresses and/or expands and/or migrates as the subject 108 moves, bends, twists, etc. Additionally, or alternatively, the neurostimulation lead 904 can include one or more anchors (e.g., anchors 130) to secure the neurostimulation lead 904 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 904. For example, the one or more anchors are configured to secure the neurostimulation lead 904 to the dura, the ligamentum flavum, or other soft tissue structure(s) to prevent migration and/or movement of the neurostimulation lead 904.

Figures 15A, 15B, 15C, 15D, 15E, 15F, 15G, 15H:
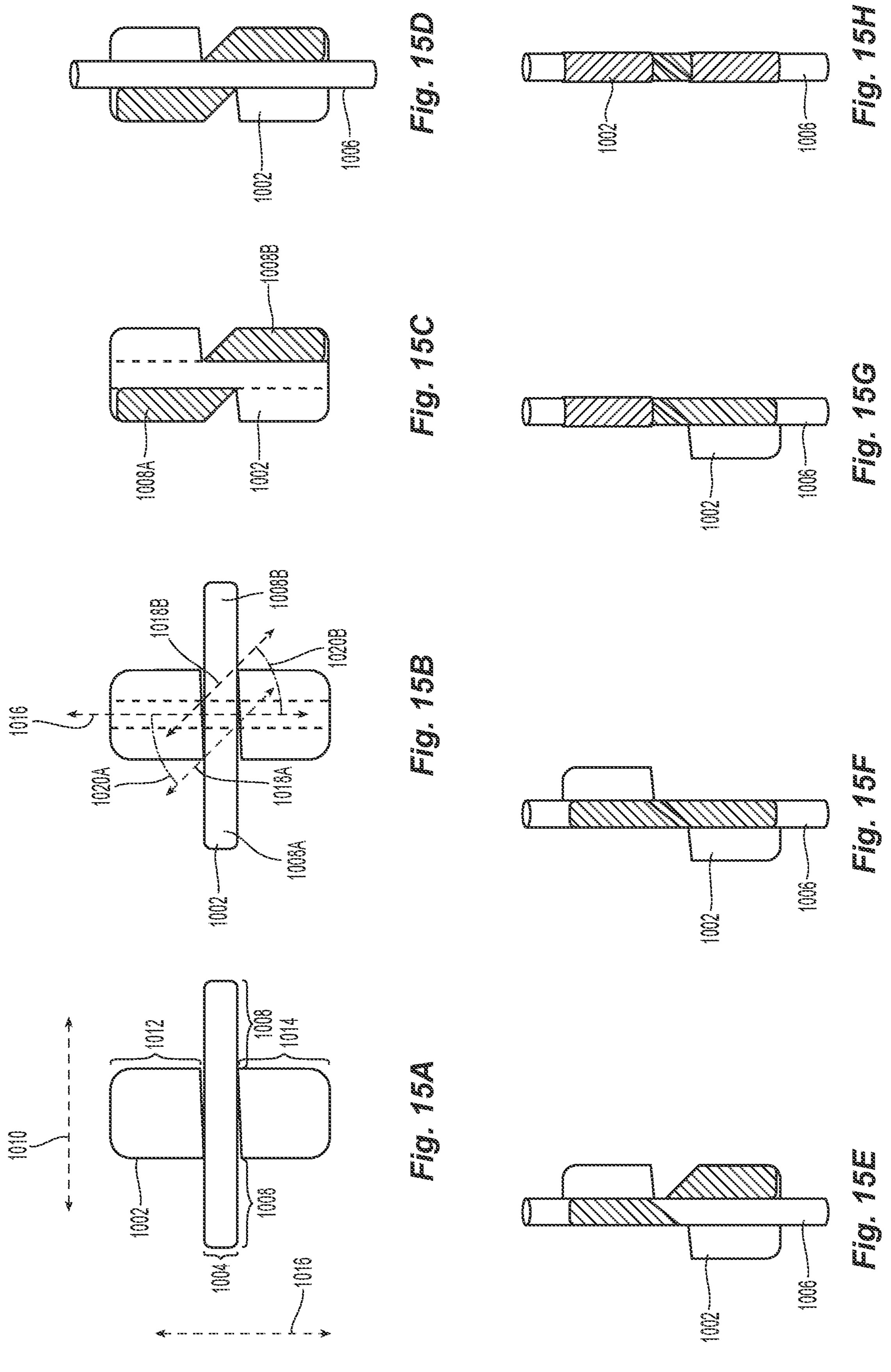
FIGS. 15A-15H are side views of a neurostimulation lead transitioning from an expanded deployed state to a collapsed delivery state, in accordance with embodiments of the present disclosure.

FIGS. 15A-15H are side views of a neurostimulation lead transitioning from an expanded deployed state to a collapsed delivery state, in accordance with embodiments of the present disclosure. In particular, FIG. 15A illustrates a neurostimulation lead 1002 in an expanded deployed configuration, FIG. 15H illustrates the neurostimulation lead 1002 in a collapsed delivery configuration, and FIGS. 15B-15G show the neurostimulation lead 1002 transitioning from the expanded deployed configuration in FIG. 15A to the collapsed delivery configuration in FIG. 15H. In aspects, the neurostimulation lead 1002 can transition from the collapsed delivery configuration to the expanded deployed configuration by arranging a delivery device over the neurostimulation lead 1002, which can collapse and/or crush the neurostimulation lead 1002.

According to certain embodiments, the neurostimulation lead 1002 can be inserted into a delivery sheath (not shown) in order to collapse the neurostimulation lead 1002 to a collapsed delivery configuration to prevent the neurostimulation lead 1002 from expanding earlier than desired. According to certain aspects, a delivery device and the neurostimulation lead 1002 can be positioned percutaneously within a subject 108 while the neurostimulation lead 1002 is in the collapsed delivery configuration (shown in FIG. 15H). For example, the neurostimulation lead 1002 can be arranged at an implantation site near the centerline of the spinal cord 133, the left and right sides of the spinal cord 133 and/or a portion of at least one dorsal root ganglion 134 within the epidural space 132. Once the neurostimulation lead 1002 is positioned at an implantation site, the delivery device can be removed (e.g., withdrawn) and the neurostimulation lead 1002 can be deployed and expanded to the expanded deployed configuration as shown in FIG. 15A. Due to the wide coverage area of the neurostimulation lead 1002, the neurostimulation lead 1002 can provide better stimulation and/or more accurate stimulation than a narrower neurostimulation lead due to being able to contact the left and right sides of the spinal cord 133 and/or at least one dorsal root ganglion 134. Further, the neurostimulation lead 1002 can be implanted percutaneously (unlike some conventional embodiments that have a wider surface area) due to the smaller profile of the neurostimulation lead 1002 while the neurostimulation lead 1002 is in the collapsed delivery configuration.

According to certain embodiments, the neurostimulation lead 1002 has the advantage of reducing material of the neurostimulation lead 1002 that is arranged around a central portion 1004 of a delivery rod 1006. For example, if the wing portions 1008 were arranged around the delivery rod 1006 along a lateral axis 1010, the neurostimulation lead 1002 would have more material arranged around the central portion 1004 of the neurostimulation lead 1002 than around a distal portion 1012 and a proximal portion 1014, resulting in a cross-sectional thickness of the central portion 1004 that is greater than a cross-sectional thickness of the distal portion 1012 and proximal portion 1014.

To reduce the cross-sectional thickness around the central portion 1004, the wing portions 1008 are arranged (e.g., folded, bent, wrapped, collapsed, crushed, etc.) at a non-zero angle relative to the lateral axis 1010 and/or a non-perpendicular angle relative to a longitudinal axis 1016. For example, in at least one embodiment, the wing 1008A can be folded, wrapped, bent, collapsed, crushed, or otherwise along a line 1018A such that the angle 1020A between the line 1018A and the longitudinal axis 1016 is greater than zero degrees and less than ninety (90) degrees. Similarly, the wing 1008B can be folded, wrapped, bent, collapsed, crushed, or otherwise along a line 1018B such that the angle 1020B between the line 1018B and the longitudinal axis 1016 is greater than zero degrees and less than ninety (90) degrees. As illustrated in FIG. 15C, by arranging the wings 1008 in such a manner, the wing 1008A is arranged next to a distal portion 1012 and the wing 1008B is arranged next to a proximal portion 1014, thereby reducing the amount of the material arranged next to the central portion 1004. In FIGS. 15C-15H, the textured portion of the neurostimulation lead 1002 represents an opposing side to the side of the neurostimulation lead 1002 shown in FIGS. 15A and 15B.

In certain embodiments, the delivery rod 1006 can be arranged along a longitudinal axis 1016 of the neurostimulation lead 1002, as shown in FIG. 15D. After which, the neurostimulation lead 1002 can be arranged around the delivery rod 1006 (e.g., folded, wrapped, bent, collapsed, crushed, etc.), as shown in FIGS. 15E-15H.

According to certain embodiments, the neurostimulation lead 1002 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, the neurostimulation lead 504 shown in FIGS. 8A-8C, the neurostimulation lead 602 shown in FIG. 9, the neurostimulation lead 702 shown in FIGS. 10 and 11, the neurostimulation lead 804 shown in FIGS. 12 and 13, and/or the neurostimulation lead 904 shown in FIG. 14. For example, the neurostimulation lead 1002 can have an array of electrodes (not shown) that is the same as or similar to the array of electrodes 112, the array of electrodes 216, the array of electrodes 310, the array of electrodes 408, the array of electrodes 512, the array of electrodes 608, the array of electrodes 710, the array of electrodes 808, and/or the array of electrodes 908. Additionally, or alternatively, the neurostimulation lead 1002 can be formed from and/or coated by a biocompatible material, such as PE, ePE, PTFE or ePTFE. Additionally, or alternatively, the neurostimulation lead 1002 can be formed in part from a shape-memory material, such as NiTi so that once the delivery rod 1006 is removed, the neurostimulation lead 1002 expands to the expanded deployed configuration shown in FIG. 15A. As such, the neurostimulation lead 1002 is in a relaxed shape when the neurostimulation lead 1002 is an in expanded deployed configuration. Additionally, or alternatively, the neurostimulation lead 1002 can include a hardening agent so that when the neurostimulation lead 1002 is in an expanded deployed configuration, a hardening agent can be added and/or applied to the neurostimulation lead 1002 to fix the neurostimulation lead 1002 in the expanded deployed configuration to reduce the likelihood the neurostimulation lead 1002 compresses and/or expands and/or migrates as the subject 108 moves, bends, twists, etc. Additionally, or alternatively, the neurostimulation lead 1002 can include one or more anchors (e.g., anchors 130) to secure the neurostimulation lead 1002 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 1002. For example, the one or more anchors are configured to secure the neurostimulation lead 1002 to the dura, the ligamentum flavum, or other soft tissue structure(s) to prevent migration and/or movement of the neurostimulation lead 1002.

Figure 16A:
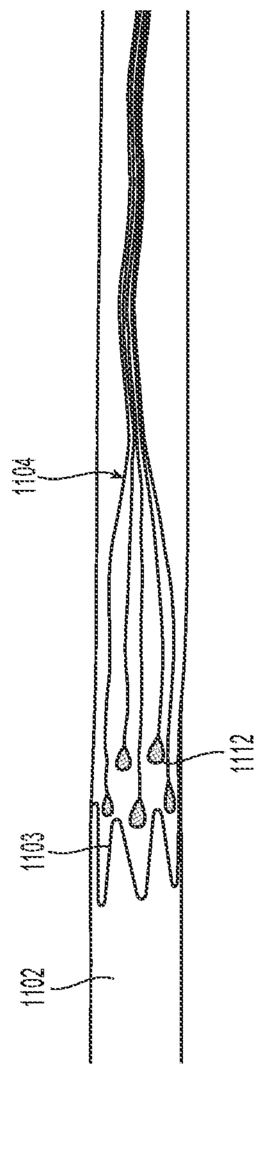
FIGS. 16A-16B are side views of an example neurostimulation lead and FIG. 16C is a perspective view of an example neurostimulation lead, in accordance with at least some embodiments of the present disclosure.
Figure 16B:
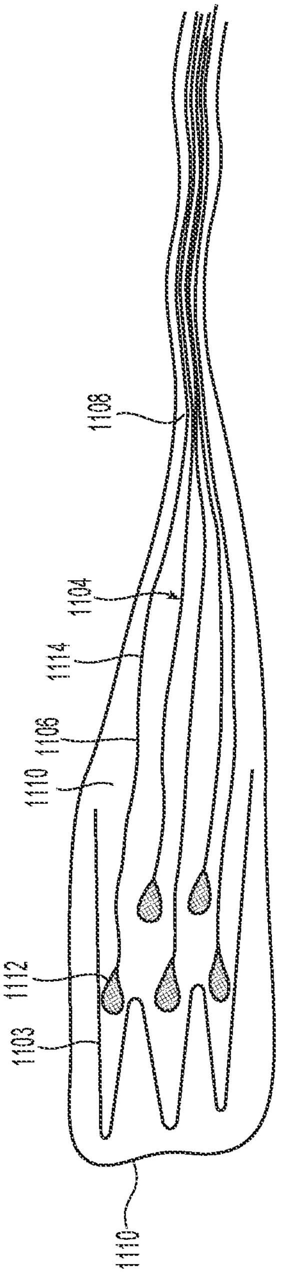
Figure 16C:
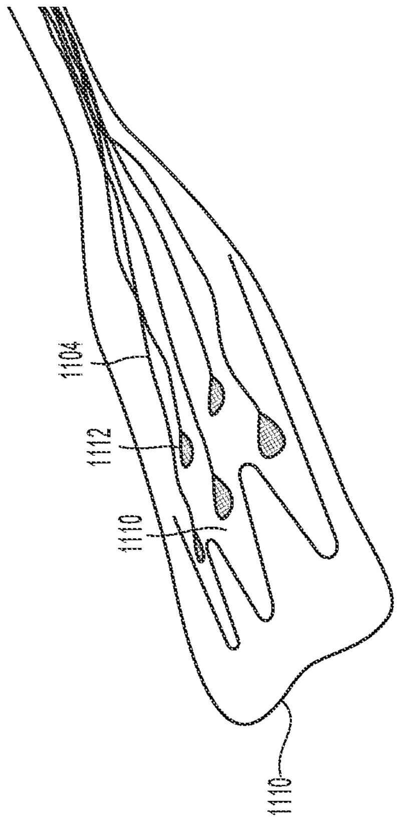

FIGS. 16A-16B are side views of an example neurostimulation lead and FIG. 16C is a perspective view of an example neurostimulation lead, in accordance with at least some embodiments of the present disclosure. In particular, FIG. 16A illustrates a delivery device 1102 including a neurostimulation lead 1104 in a collapsed delivery configuration and FIGS. 16B and 16C illustrate the neurostimulation lead 1104 in an expanded deployed configuration. According to certain embodiments, the neurostimulation lead 1104 has a greater width when the neurostimulation lead 1104 is in an expanded deployed configuration than when the neurostimulation lead 1104 is in a collapsed delivery configuration. Additionally, or alternatively, the neurostimulation lead 1104 has a cross-sectional thickness that is greater when the neurostimulation lead 1104 is in a collapsed delivery configuration than when the neurostimulation lead 1104 is in an expanded deployed configuration. According to certain embodiments, the width and the cross-sectional thickness of the neurostimulation lead 1104 can be defined the same as the width 107 and cross-sectional thickness 109 shown in FIGS. 2A and 2B. Additionally, or alternatively, in certain embodiments, the cross-sectional area of the neurostimulation lead 1104 is smaller in the collapsed delivery configuration than in the expanded deployed configuration. Additionally, or alternatively, the neurostimulation lead 1104 can be curved when the neurostimulation lead 1104 is in the expanded deployed configuration in the same or similar manner that the neurostimulation lead 106 is curved. However, these diagrams are merely examples, which should not unduly limit the scope of the claims. One of ordinary skill in the art would recognize many variations, alternatives, and modifications.

As shown in FIG. 16A, the delivery device 1102 is a sheath that surrounds and confines the neurostimulation lead 1104 to a collapsed delivery configuration to prevent the neurostimulation lead 1104 from expanding earlier than desired. According to certain aspects, the delivery device 1102 and the neurostimulation lead 1104 can be positioned percutaneously within a subject 108 while the neurostimulation lead 1104 is in the collapsed delivery configuration. For example, the neurostimulation lead 1104 can be arranged at an implantation site near the centerline of the spinal cord 133, the left and right sides of the spinal cord 133 and/or a portion of at least one dorsal root ganglion 134 within the epidural space 132. Once the neurostimulation lead 1104 is positioned at an implantation site, the delivery device 1102 can be removed (e.g., withdrawn) and the neurostimulation lead 1104 can be deployed and expanded to the expanded deployed configuration shown in FIGS. 16B and 16C. Due to the wide coverage area of the neurostimulation lead 1104, the neurostimulation lead 1104 can provide better stimulation and/or more accurate stimulation than a narrower neurostimulation lead due to being able to contact the left and right sides of the spinal cord 133 and/or at least one dorsal root ganglion 134. Further, the neurostimulation lead 1104 can be implanted percutaneously (unlike some conventional embodiments that have a wider surface area) due to the smaller profile of the neurostimulation lead 1104 while the neurostimulation lead 1104 is in the collapsed delivery configuration. Additionally, or alternatively, the neurostimulation lead 1104 can be transitioned from the expanded deployed configuration to the collapsed delivery configuration by arranging the device 1102 over the neurostimulation lead 1104.

According to certain embodiments, the neurostimulation lead 1104 can include a frame including multiple legs 1106 extending from a proximal portion 1108. In certain instances, the legs 1106 can be coated, covered, and/or wrapped with a protective material 1110, for example, High Strength Toughened Fluoropolymer (HSTF). Additionally, or alternatively, the neurostimulation lead 1104 can include an array of electrodes 1112. In certain embodiments, an electrode of the array of electrodes 1112 can be included at the end of each leg 1106. Additionally, or alternatively, one or more electrodes of the array of electrodes 1112 can be arranged at intermediate positions 1114 along one or more of the legs 1106.

According to certain embodiments, the neurostimulation lead 1104 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, and/or the neurostimulation lead 404 shown in FIGS. 7A-7B. For example, as set forth above, the neurostimulation lead 1104 can have an array of electrodes 1112 that is the same as or similar to the array of electrodes 112, the array of electrodes 216, the array of electrodes 310, and/or the array of electrodes 408. For example, the electrodes 1112 may include an enlarged area of conductive material at the end of each leg 1114. Additionally, or alternatively, the neurostimulation lead 1104 can be formed from and/or coated by a biocompatible material, such as PE, ePE, PTFE or ePTFE. Additionally, or alternatively, the neurostimulation lead 1104 can include a frame portion 1103 made from a shape-memory material, such as NiTi so that once the delivery device 1102 is removed and no longer constrains the neurostimulation lead 1104, the neurostimulation lead 1104 expands to the expanded deployed configuration shown in FIGS. 16B and 16C. As such, the frame is in a relaxed shape when the neurostimulation lead 1104 is an in expanded deployed configuration. Additionally, or alternatively, the neurostimulation lead 1104 can include a hardening agent so that when the neurostimulation lead 1104 is in an expanded deployed configuration, a hardening agent can be added and/or applied to the neurostimulation lead 1104 to fix the neurostimulation lead 1104 in the expanded deployed configuration to reduce the likelihood the neurostimulation lead 1104 compresses and/or expands and/or migrates as the subject 108 moves, bends, twists, etc. Additionally, or alternatively, the neurostimulation lead 1104 can include one or more anchors (e.g., anchors 130) to secure the neurostimulation lead 1104 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 1104. For example, the one or more anchors are configured to secure the neurostimulation lead 1104 to the dura, the ligamentum flavum, or other soft tissue structure(s) to prevent migration and/or movement of the neurostimulation lead 1104.

Figure 17:
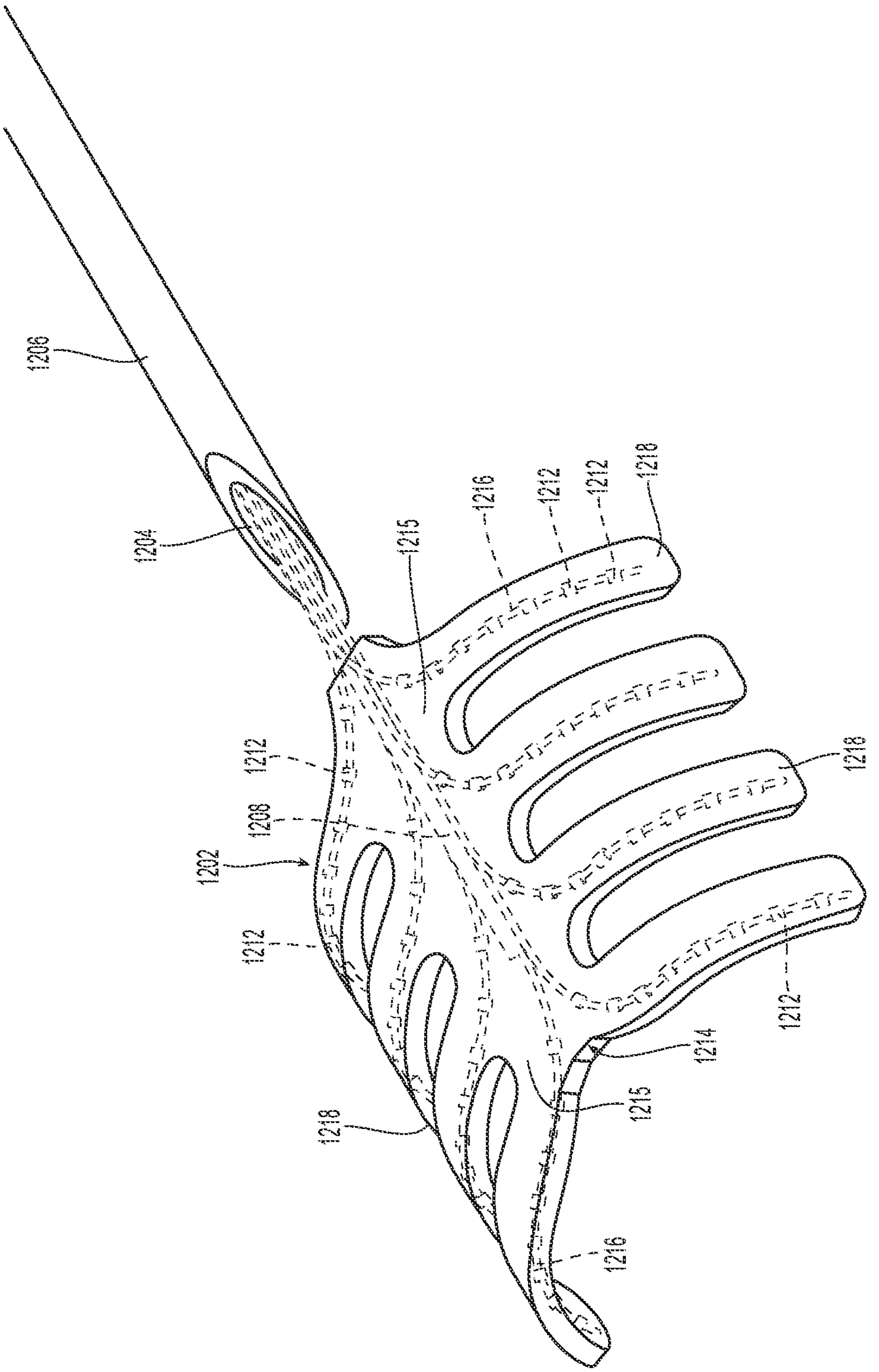
FIG. 17 is a is a perspective view of a ribbed neurostimulation lead and delivery device in accordance with at least some embodiments of the present disclosure.

FIG. 17 is a perspective view of a neurostimulation lead 1202 in accordance with embodiments of the present disclosure. As shown, the lead 1202 may be delivered through a channel 1204 in cannula such as needle 1206. An element such as spine wire 1208 can be used to push the lead 1202, when in its collapsed delivery configuration, through the needle 1206. After the lead 1202 exits the distal end of the needle 1206, it may expand to its expanded deployed configuration shown in FIG. 17. Spine wire 1208, which may for example be a NiTi wire, provides longitudinal support and/or pushability for the delivery of the lead 1202.

As shown, the neurostimulation lead 1202 includes a body portion 1214, a plurality of rib wires 1216, and one of more stimulus contacts or electrodes 1212. In the illustrated embodiments, the body portion 1214 includes a central or base portion 1215 and a plurality of ribs 1218 extending from the opposite sides of the base portion. Lead 1202 may be characterized as a fishbone array or having a fishbone shape. Each of the rib wires 1216 is located on and extends along one of the ribs 1218 of the body portion 1214. One or more electrodes 1212 are located at spaced-apart locations on each of the ribs 1218, and are shown attached to the rib wires 1216 in the illustrated embodiments. In embodiments, for example, the electrodes 1212 may be tubular elements that are slid to desired positions over the rib wires 1216. The electrodes 1212 may be formed from gold, platinum or other conductive metals or materials. A lead wire (not shown in FIG. 17) is coupled to and extends from each electrode 1212 to couple the electrode to the implantable pulse generator 104.

In some embodiments such as those shown in FIG. 17, the ribs 1218 of the body portion 1214 are discrete elements. For example, at least some of the adjacent ribs 1218 of do not include a web, membrane or other structure connecting the ribs along all or portions of their lengths. Such discrete ribs 1218 may exhibit enhanced capabilities to conform to and engage the spine and/or nerves or other body portions of subjects to which they are applied.

Body 1214 may be formed from and/or coated by biocompatible material such as PE, ePE, PTFE or ePTFE. In embodiments, for example, body 1214 can be formed from layers of such biocompatible materials that cover both sides of the electrodes 1212 an/or rib wires 1216. A backside of the body 1214, opposite the side configured to engage the spine or other portions of the body to which the lead 1202 is mounted, may be insulating. In embodiments, the electrodes 1212 may be effectively embedded within the body 1214, and clearance holes may be located in the body 1214 adjacent the electrodes 1212. For example, the electrodes 1212 may be exposed by laser etching the material of the body 1214 or by local hydrophilic treatment of the desired area. A goal is the reduce resistance/impedance through the conductive pathway, thereby reducing power consumption. In other embodiments the electrodes 1212 may be located on an outer surface of the body 1214.

According to certain embodiments, the neurostimulation lead 1202 can have the same or similar characteristics as the neurostimulation lead 106 shown in FIGS. 1-2B, the neurostimulation lead 208 shown in FIGS. 3A-5, the neurostimulation lead 304 shown in FIGS. 6A-6B, the neurostimulation lead 404 shown in FIGS. 7A-7B, the neurostimulation lead 602 shown in FIG. 9 and/or the neurostimulation lead 702 shown in FIG. 10. For example, as set forth above, the neurostimulation lead 1202 can have an array of electrodes 1212 that is the same as or similar to the array of electrodes 112, the array of electrodes 216, the array of electrodes 310, and/or the array of electrodes 408. Additionally, or alternatively, the neurostimulation lead 1202 can include a frame made from a shape-memory material, such as NiTi so that once the delivery device such as needle 1206 is removed and no longer constrains the neurostimulation lead 1202, the neurostimulation lead expands to the expanded deployed configuration shown in FIG. 17. As such, the frame is in a relaxed shape when the neurostimulation lead 1202 is an in expanded deployed configuration. In yet other embodiments the body 1214 is configured as shape-memory material to provide expansion to the expanded deployed configuration when the lead 1202 is not constrained by the delivery device such as needle 1206. Additionally, or alternatively, the neurostimulation lead 1202 can include one or more anchors (e.g., anchors 130) to secure the neurostimulation lead 1202 to a portion of the spinal column (see, e.g., FIG. 2A illustrating a cross-section of the spinal column) including, for example, to a vertebra and/or another solid structure of the spinal column and/or to a soft tissue structure to prevent migration and/or movement of the neurostimulation lead 1202. For example, the one or more anchors are configured to secure the neurostimulation lead 1202 to the dura, the ligamentum flavum, or other soft tissue structure(s) to prevent migration and/or movement of the neurostimulation lead 1202.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A neurostimulation lead, comprising:

a rod including a slot;

a body portion defined by a longitudinal axis releasably mounted in the slot of the rod and including a left portion and a right portion on opposite sides of the slot, the body portion configured to transition from a collapsed delivery configuration to an expanded deployed configuration, wherein the body portion is in a rolled configuration around the rod with both the left portion and the right portion wrapped in one of a clockwise or counterclockwise direction with respect to the longitudinal axis while the body portion is in the collapsed delivery configuration and the body portion is an unrolled configuration while the body portion is in the expanded deployed configuration and to transition from the collapsed delivery configuration to the expanded deployed configuration, the body portion is configured to unroll by unwrapping both the left portion and the right portion in the other of the clockwise or counterclockwise direction; and an array of electrodes is configured to be arranged on the body portion, wherein the array of electrodes is configured to be electrically coupled to an implantable pulse generator (IPG).

2. The neurostimulation lead of claim 1, configured to be delivered via a catheter comprising side slots and the body portion extends through the side slots to transition from the collapsed delivery configuration to the expanded deployed configuration.

3. The neurostimulation lead of claim 2, further comprising a delivery sheath around the neurostimulation lead and the catheter when the body portion is in the collapsed delivery configuration.

4. The neurostimulation lead of claim 1, wherein the body portion comprises a central spine and a plurality of side supports.

5. The neurostimulation lead of claim 1, wherein the body portion incorporates a frame composed of a shape-memory material, wherein a relaxed shape of the shape-memory material is when the frame is the expanded deployed configuration.

6. The neurostimulation lead of claim 1, wherein the body portion forms an elastomeric sleeve.

7. The neurostimulation lead of claim 1, wherein the neurostimulation lead comprises a plurality of first portions that are thicker than a second portion of the neurostimulation lead, wherein the neurostimulation lead is arranged in a pattern such that the locations of at least one of the plurality of first portions do not overlap another first portion of the plurality of first portions.

* * * * *